(12) United States Patent
Sung et al.

(10) Patent No.: US 6,376,751 B1
(45) Date of Patent: Apr. 23, 2002

(54) NUCLEIC ACIDS ENCODING EMF1 THAT CONTROL REPRODUCTIVE DEVELOPMENT IN PLANTS

(75) Inventors: Z. Renee Sung, Hillsborough, CA (US); Dominique Aubert, Essey-les-Nancy (FR); Lingjing Chen, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/415,946

(22) Filed: Oct. 8, 1999

Related U.S. Application Data

(63) Continuation-in-part of application No. 09/169,696, filed on Oct. 9, 1998, now abandoned.

(51) Int. Cl.[7] ........................ C12N 15/29; C12N 15/82; C12N 15/90; A01H 1/00; A01H 5/00
(52) U.S. Cl. .................. 800/290; 435/320.1; 435/468; 536/23.6; 800/260; 800/286; 800/298
(58) Field of Search ............................ 435/69.1, 320.1, 435/410, 419, 468; 536/23.6; 800/278, 260, 286, 290, 295, 298

(56) References Cited

FOREIGN PATENT DOCUMENTS

| WO | WO 96/11566 | 4/1996 | ............ A01H/5/00 |

OTHER PUBLICATIONS

Yang, C. et al. "Genetic Regulation of Shoot Development in Arabidopsis: Role of the EMF Genes." 1995, Developmental Biology, vol. 169, pp. 421–435.*

Dominique Aubert et al., EMF1, A Novel Protein Involved in the Control of Shoot Architecture and Flowering in Arabidopsis The Plant Cell, vol.13, pp. 1865–1875.*

Chen et al., EMF Genes Regulate Arabidopsis Inflorescence Development, *The Plant Cell*, 9:2011–2024 (Nov. 1997).

Rounsley S. D. et al, "T32A1TR TAMU, Arabidopsis thaliana genomic clone T32A1" Abstract, Jan. 1998.

Sung et al., EMF, An Arabidopsis Gene Required for Vegetative Shoot Development, *Science*, 258:1645–1647, Dec. 4, 1992.

Chou and Yang, FLD interacts with genes that affect different developmental phase transitions to regulate Arabidopsis shoot development, *The Plant Journal*, 15(2)231–242 (1998).

Salanoubat M. et al., T7 end of BAC T115 of TAMU library from strain Columbia of Arabidopsis thaliana, Abstract, Jun. 1999.

\* cited by examiner

*Primary Examiner*—Amy J. Nelson
*Assistant Examiner*—Ashwin D. Mehta
(74) *Attorney, Agent, or Firm*—Townsend and Townsend and Crew LLP

(57) ABSTRACT

The invention provides methods of modulating reproductive development in plants.

27 Claims, 1 Drawing Sheet ent (Sung et al., *Science* 258:1645–1647 (1992); Martinez-Zapater et al. In *Arabidopsis*, E. M. Meyerowitz and C. R. Somerville, eds (Cold Spring Harbor, N.Y.: Cold Spring Harbor Laboratory Press), pp 403–433 (1994); Castle, et al., *Flowering Newslet*. 19:12–19 (1995); Yang, et al., *Dev. Biol*. 169:421–435 (1995)). Based on this floral repressor concept, vegetatively growing plants must decrease EMF1 and EMF2 activities to initiate reproductive growth. It has been proposed that the floral repression genes maintain, whereas floral promotion genes inhibit, EMF1 and EMF2 activities. A balance of these gene actions would cause a gradual decline in EMF activities and determine the time of vegetative-to-reproductive transition.

SEQUENCE LISTING

```
<160> NUMBER OF SEQ ID NOS:  8

<210> SEQ ID NO 1
<211> LENGTH: 17341
<212> TYPE: DNA
<213> ORGANISM: Arabidopsis thaliana
<220> FEATURE:
<223> OTHER INFORMATION: genomic DNA (Ecotype Columbia) from CD82 clone
<221> NAME/KEY: promoter
<222> LOCATION: (1)..(3201)
<221> NAME/KEY: CDS
<222> LOCATION: join(4241..4335, 4448..4623, 4704..4823, 4903..4956,
<223> OTHER INFORMATION: EMBRYONIC FLOWER 1 (EMF1)
<221> NAME/KEY: exon
<222> LOCATION: (3202)..(3265)
<223> OTHER INFORMATION: exon 1
<221> NAME/KEY: intron
<222> LOCATION: (3266)..(4159)
<221> NAME/KEY: exon
<222> LOCATION: (4160)..(4335)
<223> OTHER INFORMATION: exon 2
<221> NAME/KEY: intron
<222> LOCATION: (4336)..(4447)
<221> NAME/KEY: exon
<222> LOCATION: (4448)..(4623)
<223> OTHER INFORMATION: exon 3
<221> NAME/KEY: intron
<222> LOCATION: (4624)..(4703)
<221> NAME/KEY: exon
<222> LOCATION: (4704)..(4823)
<223> OTHER INFORMATION: exon 4
<221> NAME/KEY: intron
<222> LOCATION: (4824)..(4902)
<221> NAME/KEY: exon
```

```
<222> LOCATION: (4903)..(4956)
<223> OTHER INFORMATION: exon 5
<221> NAME/KEY: intron
<222> LOCATION: (4957)..(5045)
<221> NAME/KEY: exon
<222> LOCATION: (5046)..(6307)
<223> OTHER INFORMATION: exon 6
<221> NAME/KEY: intron
<222> LOCATION: (6308)..(6447)
<221> NAME/KEY: exon
<222> LOCATION: (6448)..(8065)
<223> OTHER INFORMATION: exon 7
<221> NAME/KEY: intron
<222> LOCATION: (8066)..(8300)
<221> NAME/KEY: exon
<222> LOCATION: (8301)..(8648)
<223> OTHER INFORMATION: exon 8

<400> SEQUENCE: 1
```

| | | | | | |
|---|---|---|---|---|---|
| gatctcttcg | tatctggtgt | tcacccttaa | gctgaagaaa | ctcttatcat | ctaacacttc | 60 |
| tttataatta | cgaaacttca | gatattcgat | atactgttgt | tttagcttta | gaatcaatcg | 120 |
| ttgatgtata | tgtgaaaaca | tatataggtc | attagtattg | attcagaact | aattaatttt | 180 |
| ccaaaataaa | catcaagtga | gctttcttca | cagaatgtat | ctaacatttt | tttttttttgg | 240 |
| gtaaaatcta | atattttgtt | gtcgatgaat | aaaaagactt | ccaaggttcc | aacattaggt | 300 |
| tcatcgggtt | attaaataat | cgctgataat | agatacatct | aatagagaac | ttaggttaat | 360 |
| ttaacaaata | aaaatggtt | aaccaagtga | gataagttat | catctaatgg | acgtatcaac | 420 |
| aattaaagcc | aaacgattgt | ggttcccaac | tgaagttatg | agttgaaaat | taagtatttt | 480 |
| tataacggag | atcaaacgaa | ctcaaaggaa | tttgtaacat | aatataatga | atgatacaca | 540 |
| tcgatgcatg | aaagtgagta | tataagcata | taaatacatg | aataaataga | tatgatgatg | 600 |
| ttggggtgtg | tgtaagaagt | aaaaatccaa | gagttaaaaa | ggggagagag | agagaaggtt | 660 |
| gatgtggttg | tcgagatgct | aacagagagg | cacatgcaaa | gcttaaatga | tggtatcgct | 720 |
| ggtggccaaa | gcatctcctt | aaagctgtcc | ttttcatct | taagtcctct | ttttttattt | 780 |
| ccccttttgct | accgcttcac | tctttctctc | tctatatttt | gcatacatat | atttatatac | 840 |
| taatgtgtta | atcaacttgt | gtaatatacc | ttacttatgt | gcagttgtgc | acgtatgcag | 900 |
| acctaaaagt | gtatcaatta | atttatatat | atatatataa | atataatctc | ctttttttga | 960 |
| gttacaaata | cgtttgaaga | taatattcaa | aactatgtga | atcttgattt | atacggtcga | 1020 |
| gaaaaaatgt | taggttggtt | gaagataggt | tccgttccgc | ccttaatata | tcttatacaa | 1080 |
| aaagataaga | tcattacgaa | tatgtgctca | attccttttc | cataaagttg | ggtattaaat | 1140 |
| tatgaatatt | atctagaaat | tttagagggg | tgtatatagt | gtgctatttt | cgtgataaaa | 1200 |
| gtaaataatg | catccaaaat | tcaaagtgga | tcattaacac | gttttggtat | atacatcaca | 1260 |
| atttgtcaaa | cccgtaatta | attgcgccaa | acaagaaaaa | atgatcttat | ggggcaaaag | 1320 |
| taaatcacat | atatggcagt | gggaagaaaa | aaggagatta | tattttttccc | ctaaaataga | 1380 |
| ctaaagtaac | aaacctaaat | ttctctggaa | agaattatat | cataaaaacct | cgaagccgac | 1440 |
| aaaaactaag | aaaaaaaaaa | aacaatttac | cgaagaaaga | atattattaa | aaaatacagg | 1500 |
| aacaaggaga | gagaaatgtg | ttataaagga | taaagcccac | taaaggtcat | tcacttatct | 1560 |
| aactgtatac | tattattttc | ttcgaggcaa | tatataaaat | ttacttgatc | tagtaattta | 1620 |
| ttttcactaa | ggtttagtat | tcttatacat | ttgtataata | gttaacacaa | cttaacgata | 1680 |
| cttacttcta | atatgtatca | acacgtacgt | acagagccac | gtaaagaaaa | aaaacacaca | 1740 |
| cacaatcgct | gtcgaacagt | taaatcccga | atctagattt | gtattagtta | tctaatcgta | 1800 |

```
ttattgttaa ttccgaaagt agagtcaaca tccaattaat tgctttatca aatatcgaat    1860
atgcaaaagg tctaaagaaa aacaaagttt tttttttgttg ttaaactttg cttacatcat    1920
aggtatccca ttaggttggt gtaccatgtg atgattctac caccgaaaaa acagaagcca    1980
atattaaaaa atacatctat atagtacatg tacaataaca ataattaagg attattgtat    2040
tatattttaa gaaaaaaact aaatagggtt atgtgaacca gactttttt aacactttta     2100 ctgtggtaaa ctttggaaag ggaaaaaaga gtgttagggt taatatatgt atatataatt    2160
catttattgg ggaaatgggc tcatctaggg taacatcacc tacccataca attttatcat    2220
gcttttaggg cttttattta tctcactggt ccctcaattc ctccactctc tcttcccttc    2280
gcgtgaacaa cacgctccaa tgtctcccct tcgtatgtgc cgacgctcct tacctctccg    2340
cgccacggac gaaacgtgcc cacacgcgaa agtaaacgc cgtgacatcc acgcgcctag     2400
ggttttcttt tcatcaggac acaagtgaaa atgggttgt gataagaacc gcacattgcg     2460
gccacgtggt taattctcat tggtttcttg tgccccatcc tatcacacac aaaaacgtct    2520
aatacgattt aaataaaaat cgggttcttt cctaatataa agaaaacac tgagatcttt     2580 tacttaatct tgttgtttaa tttctggata ctgttcccct aagccagcta ttttctacta    2640
atgctcagat ttcttctta actaaacata tgcataaaat tttctccttt tattcactttt   2700 tgacagatac agagatacaa agaacagata cagagatgta caaatacaga tacgtgtaca    2760
caatagaagt aaaaagatac gtaactttgt ttcgtgtaat tggaaatagg cagaccagat    2820
ggtgacatgg cattgtcatg ttccatagat gagttgttct tttttttaata taaaattatt    2880 acaataaatt aataaaaaga ttattttatt gaaattaaaa cccttatatc gacgcaaagc    2940
caaacaaaaa aaaaaccctc atttcaagga taagagagct ccactttctc tctcctctcc    3000
tttctccaac agtctctctc tacaagccat aggaaaaaaa aaaagtccc cctttctctc     3060 tccctcccct ttcgtcttag ggtttctcga aaattcgcag tcaaattcta ctcatctccc    3120
gacgaatcca tccttcaagc tcatctaatc ttcttctccg tagctttctc aatctaccga    3180
tatagttttt atcccttgcc gcttaagatc gagctcgaat ctcgcaaccc cttttaatcc    3240
ctaatttctg gtcggattaa cccaggtgcg ttgtttccga catgaatctc agatgtgttt    3300
cgatttaagg tttgagctaa ggtttgatct tgttgggttg agatttggtc tgacttgtag    3360
ctgacttcgt gtcttttaag cttcactgtt catttatacg tctatcttcc tcggaaactc    3420
ttgatgttct tactttttt atttttttt tttttggg tttcgtcttc acggactatt         3480
cacgtgcgga tagatctgac ccgtattaat tggtgggtct tggttaatct ttgttaatca    3540
catacggtta atttaagtgg tttattatct tttaattttg ttctaatttt gattttaaac    3600
cctaaattac gctgattaat aatttgacct ttcttgggtt ttgtaattcc gaaattatat    3660
tgaatctggt ccgatcttct ttttcttt gctggtcatg tagataaggt tacagctttg      3720
gggtttctcg tctgtctgaa aaaccctaat tttaggtcgt ctaagtttag gtttacttac    3780
atgttaattg ttaaatgtat aaaattcact tgcacgatta attttttgtt atattagcgt    3840
aattgaattg agatgctagt atagaatttc attcttgatt ttatgtagac cttagggttt    3900 aattttttt tatttgccgt gtaattgtga agtttgatgt tggttatgaa tgttatttta     3960
tgtgggatat tcatgtgaaa tgctttaacg acgatgttat agattcgtta tatttattgc    4020
ttgaataaat ttagagttat atttggtgtc gtatatatgg aaagttaaga tttatgtctt    4080
gatatacaac aataatgtga tcattaagca caattatacg atgtgttata taacttgttt    4140
```

-continued

| | |
|---|---|
| tgatgtgttg cttttgtagc tctagttgcg gagagagtat aatggtgtat gaaagttaat | 4200 |
| catcactgag gcatagtatc tatctccttc aagcaaatca atgggatctt ccatcaagat | 4260 |
| caactcaata tccatagatc tcgcaggtgc tgccaacgag attgatatgg tgaaatgtga | 4320 |
| tcattttttcc atgcggtgag tatagtttgt tgaccttata tcatcaacct ctcttgctag | 4380 |
| agtatgttta tatagtagca agctacaaga tgaaatgaca tgaataacca gttttttcttc | 4440 |
| tctgcagtgg attcgtagct gaaactcgtg agagagacct tagaaaatgt tggccgtttt | 4500 |
| cagaagagag tgttagttta gtagaccaac aaagctatac tcttcctact ttatctgttc | 4560 |
| caaagtttag atggtggcat tgtatgagct gcatcaaaga tatagatgct catgggccaa | 4620 |
| aaggtatatc acatttccaa tattgttttt tatgtgtcta aagacgtgtc tacttgaact | 4680 |
| tatgcatttt gagttgcttg cagattgtgg actgcattca aactcaaaag ctattggaaa | 4740 |
| ctcttctgtt atcgaaagta aaagcaagtt caattcgcta actatcattg atcacgagaa | 4800 |
| agaaaagaaa actgatattg caggtatgca tctgctgagt cttggttcag tttcataatc | 4860 |
| catagcaaaa tcttaatcat tttgtattat catgtttttc agataatgct attgaggaga | 4920 |
| aagtgggtgt aaactgtgag aatgatgatc agacaggtaa agttttctct ggtcaagcaa | 4980 |
| attatgtttt ctctgatgat ctcatgatgc ggaatactaa tttcttaaag cttcaacaac | 5040 |
| tgcagctact acgtttctca agaaagcacg tggtcgacct atgggtgctt ctaatgttag | 5100 |
| gagcaagagc agaaagcttg tgagtccgga gcaggtagga aacaacagat ctaaagaaaa | 5160 |
| actaaacaaa ccatcgatgg atattagcag ctggaaagag aaacaaaatg tggatcaggc | 5220 |
| tgtgacaacg ttcggctcat ctgaaattgc tggtgtggtt gaggatacac cacctaaggc | 5280 |
| aaccaagaat cataaaggca ttcgcggtct gatggaatgc gataacgggt catcagaaag | 5340 |
| tataaatctt gctatgagtg ggttgcagcg taggaaatct cgcaaggttc gtctactcag | 5400 |
| tgagttgctt ggtaatacaa aaaccagtgg tggtagtaac atcagaaaag aagagtctgc | 5460 |
| tttgaagaag gaatcagtta gaggtcgaaa aagaaagttg ttacctgaaa acaattatgt | 5520 |
| cagccggata ttgagtacaa tgggtgcaac ctctgaaaat gcttccaaaa gttgtgactc | 5580 |
| tgatcaaggt aatagtgaat caactgatag tgggtttgac agaactccat ttaagggtaa | 5640 |
| gcagagaaac agaagatttc aggttgttga cgagtttgta ccatcacttc cttgtgaaac | 5700 |
| ttcacaagaa ggtatcaagg agcatgatgc agatcctagt aagagatcaa ctcctgcgca | 5760 |
| ctctttattc actggaaacg attctgttcc ttgtcctccg ggtactcaga aacagagag | 5820 |
| gaagctcagt ttacccaaga agaagacaaa gaagcctgta atcgataatg ggaagagcac | 5880 |
| tgtgatcagt tttagtaacg gcattgatgg aagtcaagtt aactcgcata ctggtccttc | 5940 |
| catgaacaca gtatcccaaa ctcgagactt attgaatggg aaaagggtgg gcggtttatt | 6000 |
| tgacaaccgt ttggcttcag atggatattt cagaaaatat ctctctcagg ttaatgataa | 6060 |
| gccgataaca tctttgcatt tgcaagacaa tgattatgtg aggtcaagag acgcggaacc | 6120 |
| aaactgtctt cgagatttta gttcctcttc taaatccagc tcaggtggat ggttgagaac | 6180 |
| tggagtagat attgttgact tcagaaacaa caaccacaat acaaacagat cgtctttctc | 6240 |
| gaacttgaag ctaagatacc cccttcttc tactgaagtt gcggatttat ctcgggtgct | 6300 |
| gcaaaaggta caagctttgc atctattttt cttcaatcgc catgctttct cattctgttt | 6360 |
| tccaacttgc acctattctt gtatattcca aactggtgtg cttcagtgat tggatcagga | 6420 |
| tgataacggg attgatttac ttggcaggat gcttctggtg cagatagaaa ggggaagact | 6480 |
| gttatggtcc aagaacatca tggagcacca agaagccaaa gtcacgatag aaaggagact | 6540 |

-continued

```
acgactgaag agcaaaacaa cgatgatatt ccaatggaga tagtggagct catggccaaa    6600
aaccagtacg agaggtgtct tcccgacaaa gaagaagatg ttagcaacaa acagccatca    6660
caagaaacag cacacaaatc caagaatgct ctactgattg atctcaatga aacctacgat    6720
aacgggatct cacttgagga caacaacaca tcaagaccac caaaaccgtg tagtagcaac    6780
gcaaggaggg aagaacattt tcctatggga agacagcaga actctcatga cttcttccca    6840
ataagtcagc cttatgtgcc ttctccgttt gggatctttc ctcctaccca agaaaaccga    6900
gccagctcca tccggttttc tggtcacaac tgtcagtggc ttgggaattt gccaactgtg    6960
ggtaatcaga acccttctcc atcctcattt cgggtattac gtgcttgtga tacttgccag    7020
agtgttccta atcaatacag agaagcttct catccaattt ggccatcttc catgatacca    7080
ccacagagtc aatacaagcc agtttctttt aatattaatc agtcaacaaa tccgggtacg    7140 cttttcacagg catctaacaa tgaaaataca tggaacctca actttgttgc tgccaacggg    7200
aagcaaaaat gtgggcctaa tccagaattt tcatttggct gcaaacatgc tgctggggtt    7260
agtagtagta gtagtaggcc aatagataac ttttctagtg agagctctat accggcattg    7320
catctactca gccttctgga tcctcgcctg aggtcaacga ctcccgctga ccaacacgga    7380
aacactaaat ttactaaaag acattttccg ccagccaacc agtccaaaga gtttatagag    7440
cttcaaacag gggactctag taagtcagcc tactcaacta agcagatacc ttttgatcta    7500
tacagcaaga gattcacaca agagccttcc cggaagagtt tccccatcac tccacctatt    7560
gggacgtctt cactttcatt tcaaaatgct tcatggagtc ctcatcatca agagaagaaa    7620
accaagagaa aagacacctt tgctcctgtt tacaatactc atgaaaagcc ggtgtttgca    7680
agcagcaacg accaagcgaa gttccagctg ctgggagcat cgaattccat gatgcttcct    7740
ttgaaatttc acatgacgga taagaaaag aaacaaaaga gaaaagcaga gagctgcaat    7800
aacaatgcct ctgcgggacc tgtgaagaac agttctggac ccattgtgtg cagcgtcaat    7860
agaaaccctg ctgatttcac cattcctgaa cctgggaatg tttacatgtt aacgggtgaa    7920
catctgaaag tccgtaaacg cacaaccttc aagaaaaagc cagccgtgtg taagcaggac    7980
gcaatgaagc agaccaagaa gccggtttgt ccacctacac aaaatgccta agatatacat    8040
atgtgtgtgg gagggatttg tgcaggtaag ttgctaggac tatctgtttc taattcttta    8100
gttttgggat ttacttggtt cgtctgaaat caatgactta agaaatctg caccttacta    8160 agtgtttctt tttgcattta cattagttag aactgcaaaa ggttaggttt tatgttaaag    8220 cctaggggttt agaacagagt tttatcagtc tcttcatcaa atctttgtct ccagctctaa    8280
caaaacaatt ttctctttag ttcattgtga acagatact gaggcagagg gattaacaga    8340
tggagaggga tacaaagaga gggagagaga cagagacaga gaaagagaaa gagagatcat    8400
tcctattgaa aacaagaata agtcagacag gaaacattaa aatgcaaatc ttcctcatgt    8460
tcttggtctc tggtcttaaa aacatatctt tgcttatggt ttgttcaagc atacttggga    8520
accattcagc ttgtgtatat atttaaatga ctgtagtacc cctgatagc cttgttgttt    8580 tttgtttgtt tttttgggaa atactagata cctttcagct ggcgttatat atatatttag    8640
tctttattta tactgttgtg tttaaatgtc tctgtcaggc cagccaactt ctccaaacct    8700
aagagaaacc ctcttaagtc ttaacacatt tttaatccaa aaaagactct aactgaagat    8760
tccgtaaatt aaatctctag tctgaagaaa atctgcaaa acaactttta catcaattaa    8820
aaagcttaga gtgctacaga aacgcttaag gttacttttc aacttcttaa tttacttaag    8880
```

-continued

```
aatacattga aattaagttg ggtatgttgt tgattccatg caactccgag ttttcatttg    8940
gctgactagg tgagggtgga gtagaggatc attttgaatt aagattatag gagaacaagg    9000
aatgatcgat gggaatgtga gcagatacaa ggctcaaaga ttgaaaagtt ggcggatcgg    9060
ggagaacaaa aaaagggtaa tatttgggtt aagtaagagt gagaagatgg ttcataaccg    9120
agggttagga gaacggtcat caaatgtgac ctaacgggaa aagaaaatgt ggcagattct    9180
taatataagc aaacataacc actgtggttt gtaggataaa cacatttagt ggatcggaaa    9240
actagagagt aataaaatcc taggacgatt atatgagatg gggagacgag agaaaatata    9300
tttcattgcc agttgaggaa gaggaaagga ataagtggac attcatagga agtgcttcaa    9360
cccaatagga gttaggtagt tcagcttgaa agaggagaga gtaaacaatg ttgtataggag   9420 gtttgaagaa aaaatttcgg tacgttcata ttatatataa tccatttttgt tgggacgtgt   9480 aaagatatga aaacgaagc tcgcttgtat tcaccattgt cacattggaa aatattgatt     9540
gttccctaac acttgttttg aatgaagtga ttgtgtacca cacaaaaaaa gaagtgatcg    9600
aagtataagt tattcctctt tttttttttt ttatgagata taataaagtc atatctcatt   9660
cgacatggga tttataacat gactacttgg aaactggaat gatggttgaa tccctttta    9720 ttttcagatt agtcatatat taactggtaa aattaaatcg atgggttaaa tattgtatta   9780
atcgtacatg agaaggactg ttttttcttct attgcggtta tgaaaaccttt tctattttat  9840 cgggtaaacg tatgcagggt agggattatt tttcttttt gttcagacaa cggtgttaaa    9900
cgggtaataa tccacggaat aaactaaaaa tttgcaaata cttttgaaag agttaaatat    9960
ggataaaaca gatcatttcc gtacaagacg agatcctaat aaaacattta tatccttgga  10020
aaactcatga tgaaagaata gtaacttcag tctctatatc atttcttcac cggatgacat  10080
agtttgaaca tcaaaactcg agttacatca ctataacttg agctggcgag aatctgcaaa  10140
ccctagcttg tgtataaaca aggccttcct tacaaaagta acctttggaa gggttacaat  10200
gtctttcttc tgaacacaca caatttcctt ccaaggcaca tccgtcatac ttggaagctt  10260
ctgttcctaa gagaatctca tcagaccatt cactagagaa catcttctta ggatctaact  10320
tgttctttac ttccaagaat ttatcaaagt taggtccaat cttttgcttc acgccgaaga  10380
aacccacttt cctattcttc ccccaatgcg gctttgcgcc gtgtttgaca aacgccatct  10440
gctccatctc ctccatcaca tcttggttca acctcggggt caactcatca tccgctcggt  10500
aataattaaa gtcaatgacc actgaatcct ctgtctggcc aagataagcc tttgagccct  10560
ttatgaaacg tatgaagata ccgttataga tatcgatccc gcacaatctt tcgggtttca  10620
tgtctcgtag cttcttcacg tcgagaagaa aatctctaaa cctagaaact gggaatattg  10680
cagtcgtttc ataaaagaaa agaccgttat atctcgggtc ccatgcgcaa gcgacatcaa  10740
ttctaattga agatgagtaa agacaagacc cagaagtctg gatcttgcct tgtcttccga  10800
taaccggata tccagtaaag attaaaccac tattctttaa accgttcccg attaatttct  10860
tgtatgccaa cgtagtatct gcagtggtgc attttccatt ctcattcttg ctagattcaa  10920
accccttctc tgcaacattt tcaaagccaa aactttgatt ttaaacatcc aaaccggact  10980
aattaaaccg ggaatattgg taatgtggag tcgtctagct actataagga aagaggaact  11040
aacctaatgc tcgtacccct ttagagatca agataggatt agactgaaaa ccaagaaagt  11100
cgttgactcc gttgccggag acattgaccg gtgctcggat atcgtaacgg taaacagcag  11160
tttttctaga aggataccaa gttatgtctc cgaattcgta tttttttccca tgctccataa  11220 aaatgtcttc aagtgctacg tcagatgtga agttgtacgt cacacttctc ttaaatgctt  11280
```

-continued

```
tctctatcga aagcttaacc tacagataat atggttaacg gcgttacgtc aaatatatag    11340
ttatatacaa ttgaatcaat aaaataaaaa gcactgtaag actgttaacg gcgttaagtt    11400
attgtacctt tgaaatgact cctaaaacac ccaacgacac tttaacggcg ttaagaagcg    11460
tatcatctct cccttcttcg agtctaacaa ccttcgcgaa accttctgat tggttcgccg    11520
gaaccacaag gctgattccg acaacatggt catgaaccga accacctcgt ccagaccacg    11580
aactcccgtg ggagccagta ctaatcagcc caccgatact cactccttcc cagtacggtg    11640
acgttccgat gctaaaccca gctccttcaa ctttctcgat cagctctctc aacgaaactc    11700
cagaatcagc cgtgaccgtt aacagttccg gttcaatctc gataaccgaa ttatatttcg    11760
acgtactaat tagcaatgcg tctgaacctg aaggacaagc gagtttcggt atggtgtgag    11820
agaatttggt gacggttttg actttgagat tgtgctcagc cgcgtaagca acggctttac    11880
gaaggtcttc ctccgtcgtt gggtatgtga cgttagccgc gtgacaggtt ttgcggtcag    11940
gccacgtgcc gtacgcgttg gagacggtgc agccggttag gtcgcatcga atcggtggtt    12000
gtggtggtac tgattgaacg gtccatattg taacgaagaa agatagaatt gagaactgct    12060
ggagagtatg agagtaacgc atgattattt ggagagatta tgttaatccg atctttggga    12120
tctgtgatat ttttgttttg gaggttatgt taactatgta taaatgcgtt tgaagattga    12180
aaatattgct tagaaggaaa tcaatattgc cggatctttt tatatttaag tatatgatgt    12240
atcttatgtt tttggtaagg aattaaggat attgtatagt gtgacttgtc cttttttgtc    12300
gccgttgatt tatcctaaga ggctaggaat taaaaattcg tattataaga tctgggtcaa    12360
aacctaaatt atgcaaaata atgtagggtt aagatctgaa atataatacc cactaagtat    12420
gtcatcatca ttcataaaat atatgtatag atacacttgt atagatgttg gtgtaataga    12480
tgaaaaacag tggggttaaa gagaaaaagg cggaaattga caaaataatt gatctgacaa    12540
aaaagtacaa caagggaaag catgtagtgt ttggttttaa agcgtaaaaa gactactgat    12600
gcttataatt agtttaacta tggttttatac taatttgaaa agaaaagaaa gttgatacta    12660
gctataagtt attatgtaat ccaacatcag ttgaataaaa tcgatgatat ctattttagt    12720
tgacatcatc aaaaataatt gatattgata acgtatagcg ataacgtgaa taacaccggt    12780
acgtaaaata atcgatatat gtactggaga tattatataa tttcaggact aacatagtta    12840
agcatttgag tgagggttat gattacaatt ccttgacatt ggtgattact attcagaaag    12900
ttttgagaat cagaatatta tagagtagat aatccaatac tatattttag ttggttacga    12960
cttaaaaaat tggtacaata ccattattat catggagtaa caggcaacca aaccctctaa    13020
agtcgttgtt cccctcgcc aaccgaatga ccgatacgtg tataataaaa gatgttctgg    13080
tgggaacaaa accctcatgc caattcggtc cagcttttgt aggaccgatt ttattctttt    13140
aaaaagttga tcactgagtt ggcctgactc atatagatat aaccctattt aacggtcgga    13200
tccgctaagc caaaggatca tgacggtcta aaatcttaga attagagctt ttctcaaacg    13260
tagacagtca ttaaatcgga ttaatataat caaaataatt ttatcaaatt agaatttaga    13320
ttattaaaat tttaaaccaa tactattatg tcaattttga agaaattaat tttctttagg    13380
actcaataat ttggagagct tgaccagctc cagtcataaa acatacaaaa tacaacattt    13440
tttgtgatag atggtgtaag attaattcaa gcattaatta tagataaaac catttttagta   13500 tatttagaaa tttagacaat gcaaaaagtc tttacgtcgt ttgggtgttc tagagtttga    13560
cgtagagtac ttcatttctg taagaagaaa gaagtatact tatgatatgt ggtggttttt    13620
```

-continued

```
tgttcctaac tagtatccgc tgattaatgg taattctcgc tactcgatgc tatttactta    13680
tctgttgagt gatcctaatt ctgccaaact agtatggagt gataaaaatt ctatatatta    13740
aacgatcttt tttgttctat ttggaggtta tatatatgct gtgttagaca aacgttatag    13800
gcctgttaca tatggtaata ttgtagcacc tcaatacctc attgaccggt attaccgcaa    13860
accaaattat ggtttggact ttggatcgac tactattgtt ggtcatatat aattgtatca    13920
atagtttaaa gtaatatttg gtcattaata ctgatcatgc atgcttctag atcagtagat    13980
catggttact tttatgctta aaacagtttt tgatgaaaac ctatatcact attttgctat    14040
ttacactacc gcacctggtt aagttgaata tgcattttta aattatgtgt atgtaaacgt    14100
gtgctagttc aaagttcaaa caatgttggt atatatatgt caggtgtcac ttcttattga    14160
acaatacgta ctcgtttata ccagtttgat agtcagagca aagattatgt atgattaatt    14220
cgtgttataa gcttctacct ttgtgattat tgattttttt aagtaggctt gtaacattaa    14280
ttagagtaaa attcatataa ggttctacta cttgtaatat atatatatat gtacatatat    14340
attatatagt agcatcagag ttgctatgac ttgacctggc gatgttctgg tatcgtagag    14400
atgcctccca agtatagata gagaccacct cacatgttca tgccaatagt taatgaaaat    14460
gaccaatcca tgaacatgca aaaacacatg aggttttttct aaacatatta taattgacca    14520
aataaagaga aaaaaaaaaa aacaatacat atgatcggaa tcattttggg agtttgaagg    14580
aactaaacat aatatgcatg tcgaagtcaa cttattgcaa ataattttga atgattctg    14640 aattggaaat tcatgaagct taattatttt atctaaataa gtttaatata ggtttgagtg    14700
agatatcgag attaaatgat aagagtcttt cttcgaggag acattagaat tctacacaaa    14760
aatcgaaatt aatctagtcc ttgacaatca gttttcaatt aatcaaaaac ctataaaatt    14820
caactcaaaa ccaatcgtat gaaacttcat tataccatat aatctggtta cttagcttaa    14880
atctctaccc ggcgatgttt catgcttgag agactaggta cataggacac taggagtact    14940
gcatatatgg ttacctcatg agttctcatc gtaaaatcat ccaataaaaa atggtttcct    15000
gcttaggtat acggtatacc atcttgtatc gttaaaattt atagctcagt tcgttgctaa    15060
cagtcaaata cgtcttttcca gggtaaaaaa tgtggaaatt tgttccactg taaaaaccta    15120
ataatttttg acattaataa ttaaaaggga ttataatgta atatatacaa agatagggga    15180
gacagagacg aaggcccaca catctttaac aaaagaacaa caagcccgtg accccaaaat    15240
aaaactagct ttcagattta ttattttttca tctgacataa ttgcaaccgt tagatttcat    15300
ttctcaggtc ccattctgac tcagatccaa ccgtccatat tcctctagtg tcttcaatag    15360 ttgggccccct tttcttttttc ctctcgccgt acactctcct tccagcgcca acgccaccgc    15420
ccgagccact tcttccgccg gcgccaccgc gatttcctcg ccggaatccc ctccttcgcc    15480
gcctttcccg tagaccacgg aaaggatgct tatggcgtat tctctccctc taccagccaa    15540
tctcgccatc accgctacca tcgccggcac cgtcatcgcg tgagcgcgaa cctccgccgc    15600
tccttctgcc gttgtacaca ttagctcaag agcagctaag gctcgctcca ccgctgagat    15660
ctctagtcct gccgctgttt ccaccaccgc tcgtgcggct ccagcctcga ccgccacgtg    15720
gcggtttcct tcggcgaggc agagagcgag taggatcttg gtgacgtatt ttgccgttac    15780
gatcttgttg ttgctacgaa ggcaagagac gagacctcgc atgagacccg gtggacaagt    15840
cggatcagat ggcgggtcag gtacgactac ccgctcgagt agctgtagag cgaggagctt    15900
gtcggattca gagacggatg tgaggtgaag ctctgcgatc tggaaggttt cttggagagt    15960
ggtggtgacc ggaagaggcg gtggtggagg aggtggatga ggaggaggag gagcggtgga    16020
```

```
tggagtttga tcaagatgat gaggaaagcg ccattgagtg aagctttggg aagttgaggt     16080
tgaggaggag gaagatgagg aggaagtggt ggtggcttta cggcgaggtt gctgctggtg     16140
aggagaggtt gggctgagga cggattgtgt gcagcggcgg aagaagccac aggagaagag     16200
aggacgcggt ggcgcgtggg gtttcggttt ctggtttgct ttcatcatcg ctcactaggg     16260
agactgtgtg ggactttcaa gtgaagtgga gtgaagtgaa gggaagcgtc tctgttttaa     16320
ataggaagaa aataattgat tcgaaccaaa tttgtcaggc gttacacttg tgttctccct     16380
aagattattg ctcgcattaa accattaaat aatatttatt ataatcacat gtttgtgtgt     16440
gggatggtcc ccaaacatac gaatttacga tttggacgag ggtttaagta taatggcgac     16500
atctttgttt ttttggatca atcattatct gaagacgata aaatgcaggc tgatttgggt     16560
cttaaaacat ggaatttatt gctgtttaca aaaatgaaaa ggttaaacag aggcttctat     16620
aaactttaaa ttcagaaggt gcagctcaac tctagaatgt gacaaaggtc acaaagcaag     16680
agtctgtaaa gtgtactcga tttccaaagc ctaacatcaa gaatttagct aagacaatgg     16740
ttttttcttc taagagtgcg aaaaatggtt cataaacatt ctacaatgtg aaaaagccca     16800
aagagaggaa ggattttaaa ccttacggtt ccaatcacct ccatttttcg cttagttctt     16860
tcttctctga aaggacccat gtgatgtaga tggctgcaac aagtgctaca atcgtgatca     16920
ggagaagagc gtagctgaaa tcgtcggtta gtgagtcgta ggtctttgaa ggagcaagcc     16980
ttgtgtagaa gagatccact ccataggcaa agacgtgtgt tgttgactct agcttggacg     17040
gagctgttac tatgcctctt agaccttcta ctttgtggga gtgtgtaaca tacgcctgtg     17100
gaatttgaca agtgcgttag aaactataca tcacttaatc taactgtaac caaaaccagg     17160
gattgctcag ttgtaacaaa tataaggaaa atgggtttga atgaacctga ggaatgatgg     17220
gtaatgtatc agtgagaggg atgattcctt cttctttttc agcttgagac gggttaagtg     17280
tccggcgtgg atccacaaat cgtttatcaa gtgccaatat ctaatcattc ataaaaacag     17340
t                                                                     17341

<210> SEQ ID NO 2
<211> LENGTH: 8648
<212> TYPE: DNA
<213> ORGANISM: Arabidopsis thaliana
<220> FEATURE:
<223> OTHER INFORMATION: EMF1 gene and its promoter region
<221> NAME/KEY: promoter
<222> LOCATION: (1)..(3201)
<221> NAME/KEY: CDS
<222> LOCATION: join(4241..4335, 4448..4623, 4704..4823, 4903..4956,
<223> OTHER INFORMATION: EMBRYONIC FLOWER 1 (EMF1)
<221> NAME/KEY: exon
<222> LOCATION: (3202)..(3265)
<223> OTHER INFORMATION: exon 1
<221> NAME/KEY: intron
<222> LOCATION: (3266)..(4159)
<221> NAME/KEY: exon
<222> LOCATION: (4160)..(4335)
<223> OTHER INFORMATION: exon 2
<221> NAME/KEY: intron
<222> LOCATION: (4336)..(4447)
<221> NAME/KEY: exon
<222> LOCATION: (4448)..(4623)
<223> OTHER INFORMATION: exon 3
<221> NAME/KEY: intron
<222> LOCATION: (4624)..(4703)
<221> NAME/KEY: exon
<222> LOCATION: (4704)..(4823)
<223> OTHER INFORMATION: exon 4
<221> NAME/KEY: intron
<222> LOCATION: (4824)..(4902)
```

```
<221> NAME/KEY: exon
<222> LOCATION: (4903)..(4956)
<223> OTHER INFORMATION: exon 5
<221> NAME/KEY: intron
<222> LOCATION: (4957)..(5045)
<221> NAME/KEY: exon
<222> LOCATION: (5046)..(6307)
<223> OTHER INFORMATION: exon 6
<221> NAME/KEY: intron
<222> LOCATION: (6308)..(6447)
<221> NAME/KEY: exon
<222> LOCATION: (6448)..(8065)
<223> OTHER INFORMATION: exon 7
<221> NAME/KEY: intron
<222> LOCATION: (8066)..(8300)
<221> NAME/KEY: exon
<222> LOCATION: (8301)..(8648)
<223> OTHER INFORMATION: exon 8

<400> SEQUENCE: 2
```

| | | | | | |
|---|---|---|---|---|---|
| gatctcttcg | tatctggtgt | tcacccttaa | gctgaagaaa | ctcttatcat | ctaacacttc | 60 |
| tttataatta | cgaaacttca | gatattcgat | atactgttgt | tttagcttta | gaatcaatcg | 120 |
| ttgatgtata | tgtgaaaaca | tatataggtc | attagtattg | attcagaact | aattaatttt | 180 |
| ccaaaataaa | catcaagtga | gctttcttca | cagaatgtat | ctaacatttt | ttttttttgg | 240 |
| gtaaaatcta | atattttgtt | gtcgatgaat | aaaaagactt | ccaaggttcc | aacattaggt | 300 |
| tcatcgggtt | attaaataat | cgctgataat | agatacatct | aatagagaac | ttaggttaat | 360 |
| ttaacaaata | aaaaatggtt | aaccaagtga | gataagttat | catctaatgg | acgtatcaac | 420 |
| aattaaagcc | aaacgattgt | ggttcccaac | tgaagttatg | agttgaaaat | taagtatttt | 480 |
| tataacggag | atcaaacgaa | ctcaaaggaa | tttgtaacat | aatataatga | atgatacaca | 540 |
| tcgatgcatg | aaagtgagta | tataagcata | taaatacatg | aataaataga | tatgatgatg | 600 |
| ttggggtgtg | tgtaagaagt | aaaaatccaa | gagttaaaaa | ggggagagag | agagaaggtt | 660 |
| gatgtggttg | tcgagatgct | aacagagagg | cacatgcaaa | gcttaaatga | tggtatcgct | 720 |
| ggtggccaaa | gcatctcctt | aaagctgtcc | tttttcatct | taagtcctct | ttttttattt | 780 |
| ccccttttgct | accgcttcac | tctttctctc | tctatatttt | gcatacatat | atttatatac | 840 |
| taatgtgtta | atcaacttgt | gtaatatacc | ttacttatgt | gcagttgtgc | acgtatgcag | 900 |
| acctaaaagt | gtatcaatta | atttatatat | atatatataa | atataatctc | ctttttttga | 960 |
| gttacaaata | cgtttgaaga | taatattcaa | aactatgtga | atcttgattt | atacggtcga | 1020 |
| gaaaaaatgt | taggttggtt | gaagataggt | tccgttccgc | ccttaatata | tcttatacaa | 1080 |
| aaagataaga | tcattacgaa | tatgtgctca | attccttttc | cataaagttg | ggtattaaat | 1140 |
| tatgaatatt | atctagaaat | tttagagggg | tgtatatagt | gtgctatttt | cgtgataaaa | 1200 |
| gtaaataatg | catccaaaat | tcaaagtgga | tcattaacac | gttttggtat | atacatcaca | 1260 |
| atttgtcaaa | cccgtaatta | attgcgccaa | acaagaaaaa | atgatcttat | ggggcaaaag | 1320 |
| taaatcacat | atatggcagt | gggaagaaaa | aaggagatta | tattttttccc | ctaaaataga | 1380 |
| ctaaagtaac | aaacctaaat | ttctctggaa | agaattatat | cataaaacct | cgaagccgac | 1440 |
| aaaaactaag | aaaaaaaaaa | aacaatttac | cgaagaaaga | atattattaa | aaaatacagg | 1500 |
| aacaaggaga | gagaaatgtg | ttataaagga | taaagcccac | taaaggtcat | tcacttatct | 1560 |
| aactgtatac | tattattttc | ttcgaggcaa | tatataaaat | ttacttgatc | tagtaattta | 1620 |
| ttttcactaa | ggtttagtat | tcttatacat | ttgtataata | gttaacacaa | cttaacgata | 1680 |
| cttacttcta | atatgtatca | acacgtacgt | acagagccac | gtaaagaaaa | aaaacacaca | 1740 |

```
cacaatcgct gtcgaacagt taaatcccga atctagattt gtattagtta tctaatcgta    1800
ttattgttaa ttccgaaagt agagtcaaca tccaattaat tgctttatca aatatcgaat    1860
atgcaaaagg tctaaagaaa aacaaagttt tttttttgttg ttaaactttg cttacatcat    1920
aggtatccca ttaggttggt gtaccatgtg atgattctac caccgaaaaa acagaagcca    1980
atattaaaaa atacatctat atagtacatg tacaataaca ataattaagg attattgtat    2040
tatattttaa gaaaaaaact aaatagggtt atgtgaacca gactttttt aacactttta    2100 ctgtggtaaa ctttggaaag ggaaaaaaga gtgttagggt taatatatgt atatataatt    2160
catttattgg ggaaatgggc tcatctaggg taacatcacc tacccataca attttatcat    2220
gcttttaggc cttttattta tctcactggt ccctcaattc ctccactctc tcttcccttc    2280
gcgtgaacaa cacgctccaa tgtctcccct tcgtatgtgc cgacgctcct tacctctccg    2340
cgccacggac gaaacgtgcc cacacgcgaa agtaaacgc cgtgacatcc acgcgcctag    2400
ggttttcttt tcatcaggac acaagtgaaa atgggttgt gataagaacc gcacattgcg    2460
gccacgtggt taattctcat tggtttcttg tgccccatcc tatcacacac aaaaacgtct    2520
aatacgattt aaataaaaat cgggttcttt cctaatataa agaaaaacac tgagatcttt    2580
tacttaatct tgttgtttaa tttctggata ctgttcccct aagccagcta ttttctacta    2640
atgctcagat ttcttttctta actaaacata tgcataaaat tttctccttt tattcacttt    2700
tgacagatac agatacaa agaacagata cagagatgta caaatacaga tacgtgtaca    2760
caatagaagt aaaagatac gtaactttgt ttcgtgtaat tggaaatagg cagaccagat    2820
ggtgacatgg cattgtcatg ttccatagat gagttgttct tttttaata taaaattatt    2880 acaataaatt aataaaaaga ttattttatt gaaattaaaa cccttatatc gacgcaaagc    2940
caaacaaaaa aaaacccctc atttcaagga taagagagct ccactttctc tctcctctcc    3000
tttctccaac agtctctctc tacaagccat aggaaaaaaa aaaagtccc cctttctctc    3060 tccctcccct ttcgtcttag ggtttctcga aaattcgcag tcaaattcta ctcatctccc    3120
gacgaatcca tccttcaagc tcatctaatc ttcttctccg tagctttctc aatctaccga    3180
tatagttttt atcccttgcc gcttaagatc gagctcgaat ctcgcaaccc cttttaatcc    3240
ctaatttctg tcggattaa cccaggtgcg ttgtttccga catgaatctc agatgtgttt    3300
cgatttaagg tttgagctaa ggtttgatct tgttgggttg agatttggtc tgacttgtag    3360
ctgacttcgt gtcttttaag cttcactgtt catttatacg tctatcttcc tcggaaactc    3420
ttgatgttct tacttttttt atttttttt tttttgggg tttcgtcttc acggactatt    3480
cacgtgcgga tagatctgac ccgtattaat tggtgggtct tggttaatct tgttaatca    3540 catacggtta atttaagtgg tttattatct tttaattttg ttctaatttt gattttaaac    3600
cctaaattac gctgattaat aatttgacct ttccttgggtt ttgtaattcc gaaattatat    3660
tgaatctggt ccgatcttct ttttttcttt gctggtcatg tagataaggt tacagctttg    3720
gggtttctcg tctgtctgaa aaaccctaat tttaggtcgt ctaagtttag gtttacttac    3780
atgttaattg ttaaatgtat aaaattcact tgcacgatta attttttgtt atattagcgt    3840
aattgaattg agatgctagt atagaatttc attcttgatt ttatgtagac cttagggttt    3900
aatttttttt tatttgccgt gtaattgtga agtttgatgt tggttatgaa tgttatttta    3960
tgtgggatat tcatgtgaaa tgctttaacg acgatgttat agattcgtta tatttattgc    4020
ttgaataaat ttagagttat atttggtgtc gtatatatgg aaagttaaga tttatgtctt    4080
gatatacaac aataatgtga tcattaagca caattatacg atgtgttata taacttgttt    4140
```

```
                                                        -continued tgatgtgttg cttttgtagc tctagttgcg gagagagtat aatggtgtat gaaagttaat         4200
catcactgag gcatagtatc tatctccttc aagcaaatca atg gga tct tcc atc         4255
                                            Met Gly Ser Ser Ile
                                             1               5 aag atc aac tca ata tcc ata gat ctc gca ggt gct gcc aac gag att         4303
Lys Ile Asn Ser Ile Ser Ile Asp Leu Ala Gly Ala Ala Asn Glu Ile
         10                  15                  20 gat atg gtg aaa tgt gat cat ttt tcc atg cg gtgagtatag                   4345
Asp Met Val Lys Cys Asp His Phe Ser Met Arg
         25                  30 tttgttgacc ttatatcatc aacctctctt gctagagtat gtttatatag tagcaagcta        4405
caagatgaaa tgacatgaat aaccagtttt tcttctctgc ag t gga ttc gta gct        4460
                                               Gly Phe Val Ala
                                                            35 gaa act cgt gag aga gac ctt aga aaa tgt tgg ccg ttt tca gaa gag         4508
Glu Thr Arg Glu Arg Asp Leu Arg Lys Cys Trp Pro Phe Ser Glu Glu
             40                  45                  50 agt gtt agt tta gta gac caa caa agc tat act ctt cct act tta tct         4556
Ser Val Ser Leu Val Asp Gln Gln Ser Tyr Thr Leu Pro Thr Leu Ser
         55                  60                  65 gtt cca aag ttt aga tgg tgg cat tgt atg agc tgc atc aaa gat ata         4604
Val Pro Lys Phe Arg Trp Trp His Cys Met Ser Cys Ile Lys Asp Ile
 70                  75                  80 gat gct cat ggg cca aaa g gtatatcaca tttccaatat tgttttttat              4653
Asp Ala His Gly Pro Lys
 85                  90 gtgtctaaag acgtgtctac ttgaacttat gcatttgag ttgcttgcag    at tgt         4708
                                                        Asp Cys gga ctg cat tca aac tca aaa gct att gga aac tct tct gtt atc gaa         4756
Gly Leu His Ser Asn Ser Lys Ala Ile Gly Asn Ser Ser Val Ile Glu
             95                  100                 105 agt aaa agc aag ttc aat tcg cta act atc att gat cac gag aaa gaa         4804
Ser Lys Ser Lys Phe Asn Ser Leu Thr Ile Ile Asp His Glu Lys Glu
         110                 115                 120 aag aaa act gat att gca g gtatgcatct gctgagtctt ggttcagttt              4853
Lys Lys Thr Asp Ile Ala
125             130 cataatccat agcaaaatct taatcatttt gtattatcat gtttttcag    at aat         4907
                                                        Asp Asn
gct att gag gag aaa gtg ggt gta aac tgt gag aat gat gat cag aca g       4956
Ala Ile Glu Glu Lys Val Gly Val Asn Cys Glu Asn Asp Asp Gln Thr
         135                 140                 145 gtaaagtttt ctctggtcaa gcaaattatg ttttctctga tgatctcatg atgcggaata       5016
ctaatttctt aaagcttcaa caactgcag   ct act acg ttt ctc aag aaa gca        5068
                                  Ala Thr Thr Phe Leu Lys Lys Ala
                                           150                 155 cgt ggt cga cct atg ggt gct tct aat gtt agg agc aag agc aga aag         5116
Arg Gly Arg Pro Met Gly Ala Ser Asn Val Arg Ser Lys Ser Arg Lys
             160                 165                 170 ctt gtg agt ccg gag cag gta gga aac aac aga tct aaa gaa aaa cta         5164
Leu Val Ser Pro Glu Gln Val Gly Asn Asn Arg Ser Lys Glu Lys Leu
         175                 180                 185 aac aaa cca tcg atg gat att agc agc tgg aaa gag aaa caa aat gtg         5212
Asn Lys Pro Ser Met Asp Ile Ser Ser Trp Lys Glu Lys Gln Asn Val
         190                 195                 200 gat cag gct gtg aca acg ttc ggc tca tct gaa att gct ggt gtg gtt         5260
Asp Gln Ala Val Thr Thr Phe Gly Ser Ser Glu Ile Ala Gly Val Val
205                 210                 215                 220
```

```
gag gat aca cca cct aag gca acc aag aat cat aaa ggc att cgc ggt    5308
Glu Asp Thr Pro Pro Lys Ala Thr Lys Asn His Lys Gly Ile Arg Gly
                225                 230                 235 ctg atg gaa tgc gat aac ggg tca tca gaa agt ata aat ctt gct atg    5356
Leu Met Glu Cys Asp Asn Gly Ser Ser Glu Ser Ile Asn Leu Ala Met
            240                 245                 250 agt ggg ttg cag cgt agg aaa tct cgc aag gtt cgt cta ctc agt gag    5404
Ser Gly Leu Gln Arg Arg Lys Ser Arg Lys Val Arg Leu Leu Ser Glu
        255                 260                 265 ttg ctt ggt aat aca aaa acc agt ggt ggt agt aac atc aga aaa gaa    5452
Leu Leu Gly Asn Thr Lys Thr Ser Gly Gly Ser Asn Ile Arg Lys Glu
    270                 275                 280 gag tct gct ttg aag aag gaa tca gtt aga ggt cga aaa aga aag ttg    5500
Glu Ser Ala Leu Lys Lys Glu Ser Val Arg Gly Arg Lys Arg Lys Leu
285                 290                 295                 300 tta cct gaa aac aat tat gtc agc cgg ata ttg agt aca atg ggt gca    5548
Leu Pro Glu Asn Asn Tyr Val Ser Arg Ile Leu Ser Thr Met Gly Ala
                305                 310                 315 acc tct gaa aat gct tcc aaa agt tgt gac tct gat caa ggt aat agt    5596
Thr Ser Glu Asn Ala Ser Lys Ser Cys Asp Ser Asp Gln Gly Asn Ser
            320                 325                 330 gaa tca act gat agt ggg ttt gac aga act cca ttt aag ggt aag cag    5644
Glu Ser Thr Asp Ser Gly Phe Asp Arg Thr Pro Phe Lys Gly Lys Gln
        335                 340                 345 aga aac aga aga ttt cag gtt gtt gac gag ttt gta cca tca ctt cct    5692
Arg Asn Arg Arg Phe Gln Val Val Asp Glu Phe Val Pro Ser Leu Pro
    350                 355                 360 tgt gaa act tca caa gaa ggt atc aag gag cat gat gca gat cct agt    5740
Cys Glu Thr Ser Gln Glu Gly Ile Lys Glu His Asp Ala Asp Pro Ser
365                 370                 375                 380 aag aga tca act cct gcg cac tct tta ttc act gga aac gat tct gtt    5788
Lys Arg Ser Thr Pro Ala His Ser Leu Phe Thr Gly Asn Asp Ser Val
                385                 390                 395 cct tgt cct ccg ggt act cag aga aca gag agg aag ctc agt tta ccc    5836
Pro Cys Pro Pro Gly Thr Gln Arg Thr Glu Arg Lys Leu Ser Leu Pro
            400                 405                 410 aag aag aag aca aag aag cct gta atc gat aat ggg aag agc act gtg    5884
Lys Lys Lys Thr Lys Lys Pro Val Ile Asp Asn Gly Lys Ser Thr Val
        415                 420                 425 atc agt ttt agt aac ggc att gat gga agt caa gtt aac tcg cat act    5932
Ile Ser Phe Ser Asn Gly Ile Asp Gly Ser Gln Val Asn Ser His Thr
    430                 435                 440 ggt cct tcc atg aac aca gta tcc caa act cga gac tta ttg aat ggg    5980
Gly Pro Ser Met Asn Thr Val Ser Gln Thr Arg Asp Leu Leu Asn Gly
445                 450                 455                 460 aaa agg gtg ggc ggt tta ttt gac aac cgt ttg gct tca gat gga tat    6028
Lys Arg Val Gly Gly Leu Phe Asp Asn Arg Leu Ala Ser Asp Gly Tyr
                465                 470                 475 ttc aga aaa tat ctc tct cag gtt aat gat aag ccg ata aca tct ttg    6076
Phe Arg Lys Tyr Leu Ser Gln Val Asn Asp Lys Pro Ile Thr Ser Leu
            480                 485                 490 cat ttg caa gac aat gat tat gtg agg tca aga gac gcg gaa cca aac    6124
His Leu Gln Asp Asn Asp Tyr Val Arg Ser Arg Asp Ala Glu Pro Asn
        495                 500                 505 tgt ctt cga gat ttt agt tcc tct tct aaa tcc agc tca ggt gga tgg    6172
Cys Leu Arg Asp Phe Ser Ser Ser Ser Lys Ser Ser Ser Gly Gly Trp
    510                 515                 520 ttg aga act gga gta gat att gtt gac ttc aga aac aac aac cac aat    6220
Leu Arg Thr Gly Val Asp Ile Val Asp Phe Arg Asn Asn Asn His Asn
```

```
              525                 530                 535                 540
aca aac aga tcg tct ttc tcg aac ttg aag cta aga tac ccc cct tct       6268
Thr Asn Arg Ser Ser Phe Ser Asn Leu Lys Leu Arg Tyr Pro Pro Ser
                    545                 550                 555 tct act gaa gtt gcg gat tta tct cgg gtg ctg caa aag gtacaagctt        6317
Ser Thr Glu Val Ala Asp Leu Ser Arg Val Leu Gln Lys
        560                 565 tgcatctatt tttcttcaat cgccatgctt tctcattctg ttttccaact tgcacctatt    6377
cttgtatatt ccaaactggt gtgcttcagt gattggatca ggatgataac gggattgatt    6437
tacttggcag gat gct tct ggt gca gat aga aag ggg aag act gtt atg       6486
              Asp Ala Ser Gly Ala Asp Arg Lys Gly Lys Thr Val Met
                              570                 575                 580 gtc caa gaa cat cat gga gca cca aga agc caa agt cac gat aga aag       6534
Val Gln Glu His His Gly Ala Pro Arg Ser Gln Ser His Asp Arg Lys
            585                 590                 595 gag act acg act gaa gag caa aac aac gat gat att cca atg gag ata       6582
Glu Thr Thr Thr Glu Glu Gln Asn Asn Asp Asp Ile Pro Met Glu Ile
        600                 605                 610 gtg gag ctc atg gcc aaa aac cag tac gag agg tgt ctt ccc gac aaa       6630
Val Glu Leu Met Ala Lys Asn Gln Tyr Glu Arg Cys Leu Pro Asp Lys
615                 620                 625                 630 gaa gaa gat gtt agc aac aaa cag cca tca caa gaa aca gca cac aaa       6678
Glu Glu Asp Val Ser Asn Lys Gln Pro Ser Gln Glu Thr Ala His Lys
                635                 640                 645 tcc aag aat gct cta ctg att gat ctc aat gaa acc tac gat aac ggg       6726
Ser Lys Asn Ala Leu Leu Ile Asp Leu Asn Glu Thr Tyr Asp Asn Gly
            650                 655                 660 atc tca ctt gag gac aac aac aca tca aga cca cca aaa ccg tgt agt       6774
Ile Ser Leu Glu Asp Asn Asn Thr Ser Arg Pro Pro Lys Pro Cys Ser
        665                 670                 675 agc aac gca agg agg gaa gaa cat ttt cct atg gga aga cag cag aac       6822
Ser Asn Ala Arg Arg Glu Glu His Phe Pro Met Gly Arg Gln Gln Asn
    680                 685                 690 tct cat gac ttc ttc cca ata agt cag cct tat gtg cct tct ccg ttt       6870
Ser His Asp Phe Phe Pro Ile Ser Gln Pro Tyr Val Pro Ser Pro Phe
695                 700                 705                 710 ggg atc ttt cct cct acc caa gaa aac cga gcc agc tcc atc cgg ttt       6918
Gly Ile Phe Pro Pro Thr Gln Glu Asn Arg Ala Ser Ser Ile Arg Phe
                715                 720                 725 tct ggt cac aac tgt cag tgg ctt ggg aat ttg cca act gtg ggt aat       6966
Ser Gly His Asn Cys Gln Trp Leu Gly Asn Leu Pro Thr Val Gly Asn
            730                 735                 740 cag aac cct tct cca tcc tca ttt cgg gta tta cgt gct tgt gat act       7014
Gln Asn Pro Ser Pro Ser Ser Phe Arg Val Leu Arg Ala Cys Asp Thr
        745                 750                 755 tgc cag agt gtt cct aat caa tac aga gaa gct tct cat cca att tgg       7062
Cys Gln Ser Val Pro Asn Gln Tyr Arg Glu Ala Ser His Pro Ile Trp
    760                 765                 770 cca tct tcc atg ata cca cca cag agt caa tac aag cca gtt tct tta       7110
Pro Ser Ser Met Ile Pro Pro Gln Ser Gln Tyr Lys Pro Val Ser Leu
775                 780                 785                 790 aat att aat cag tca aca aat ccg ggt acg ctt tca cag gca tct aac       7158
Asn Ile Asn Gln Ser Thr Asn Pro Gly Thr Leu Ser Gln Ala Ser Asn
                795                 800                 805 aat gaa aat aca tgg aac ctc aac ttt gtt gct gcc aac ggg aag caa       7206
Asn Glu Asn Thr Trp Asn Leu Asn Phe Val Ala Ala Asn Gly Lys Gln
            810                 815                 820 aaa tgt ggg cct aat cca gaa ttt tca ttt ggc tgc aaa cat gct gct       7254
```

```
              Lys Cys Gly Pro Asn Pro Glu Phe Ser Phe Gly Cys Lys His Ala Ala
                          825                 830                 835 ggg gtt agt agt agt agt agt agg cca ata gat aac ttt tct agt gag                 7302
Gly Val Ser Ser Ser Ser Ser Arg Pro Ile Asp Asn Phe Ser Ser Glu
840                         845                 850 agc tct ata ccg gca ttg cat cta ctc agc ctt ctg gat cct cgc ctg                 7350
Ser Ser Ile Pro Ala Leu His Leu Leu Ser Leu Leu Asp Pro Arg Leu
855                 860                 865                 870 agg tca acg act ccc gct gac caa cac gga aac act aaa ttt act aaa                 7398
Arg Ser Thr Thr Pro Ala Asp Gln His Gly Asn Thr Lys Phe Thr Lys
                    875                 880                 885 aga cat ttt ccg cca gcc aac cag tcc aaa gag ttt ata gag ctt caa                 7446
Arg His Phe Pro Pro Ala Asn Gln Ser Lys Glu Phe Ile Glu Leu Gln
            890                 895                 900 aca ggg gac tct agt aag tca gcc tac tca act aag cag ata cct ttt                 7494
Thr Gly Asp Ser Ser Lys Ser Ala Tyr Ser Thr Lys Gln Ile Pro Phe
        905                 910                 915 gat cta tac agc aag aga ttc aca caa gag cct tcc cgg aag agt ttc                 7542
Asp Leu Tyr Ser Lys Arg Phe Thr Gln Glu Pro Ser Arg Lys Ser Phe
    920                 925                 930 ccc atc act cca cct att ggg acg tct tca ctt tca ttt caa aat gct                 7590
Pro Ile Thr Pro Pro Ile Gly Thr Ser Ser Leu Ser Phe Gln Asn Ala
935                 940                 945                 950 tca tgg agt cct cat cat caa gag aag aaa acc aag aga aaa gac acc                 7638
Ser Trp Ser Pro His His Gln Glu Lys Lys Thr Lys Arg Lys Asp Thr
                    955                 960                 965 ttt gct cct gtt tac aat act cat gaa aag ccg gtg ttt gca agc agc                 7686
Phe Ala Pro Val Tyr Asn Thr His Glu Lys Pro Val Phe Ala Ser Ser
            970                 975                 980 aac gac caa gcg aag ttc cag ctg ctg gga gca tcg aat tcc atg atg                 7734
Asn Asp Gln Ala Lys Phe Gln Leu Leu Gly Ala Ser Asn Ser Met Met
        985                 990                 995 ctt cct ttg aaa ttt cac atg acg gat aaa gaa aag aaa caa aag aga                 7782
Leu Pro Leu Lys Phe His Met Thr Asp Lys Glu Lys Lys Gln Lys Arg
    1000                1005                1010 aaa gca gag agc tgc aat aac aat gcc tct gcg gga cct gtg aag aac                 7830
Lys Ala Glu Ser Cys Asn Asn Asn Ala Ser Ala Gly Pro Val Lys Asn
1015                1020                1025                1030 agt tct gga ccc att gtg tgc agc gtc aat aga aac cct gct gat ttc                 7878
Ser Ser Gly Pro Ile Val Cys Ser Val Asn Arg Asn Pro Ala Asp Phe
                    1035                1040                1045 acc att cct gaa cct ggg aat gtt tac atg tta acg ggt gaa cat ctg                 7926
Thr Ile Pro Glu Pro Gly Asn Val Tyr Met Leu Thr Gly Glu His Leu
            1050                1055                1060 aaa gtc cgt aaa cgc aca acc ttc aag aaa aag cca gcc gtg tgt aag                 7974
Lys Val Arg Lys Arg Thr Thr Phe Lys Lys Lys Pro Ala Val Cys Lys
        1065                1070                1075 cag gac gca atg aag cag acc aag aag ccg gtt tgt cca cct aca caa                 8022
Gln Asp Ala Met Lys Gln Thr Lys Lys Pro Val Cys Pro Pro Thr Gln
    1080                1085                1090 aat gcc taaagatata caatgtgtgt gggagggatt tgtgcaggta agttgctagg                  8078
Asn Ala
1095 actatctgtt tctaattctt tagttttggg atttacttgg ttcgtctgaa atcaatgact              8138 taaagaaatc tgcaccttac taagtgtttc tttttgcatt tacattagtt agaactgcaa              8198 aaggttaggt tttatgttaa agcctagggt ttagaacaga gttttatcag tctcttcatc              8258 aaatctttgt ctccagctct aacaaaacaa ttttctcttt agttcattgt gaaacagata              8318
```

-continued

```
ctgaggcaga gggattaaca gatggagagg gatacaaaga gagggagaga gacagagaca   8378
gagaaagaga aagagagatc attcctattg aaaacaagaa taagtcagac aggaaacatt   8438
aaaatgcaaa tcttcctcat gttcttggtc tctggtctta aaaacatatc tttgcttatg   8498
gtttgttcaa gcatacttgg gaaccattca gcttgtgtat atatttaaat gactgtagta   8558
cccctgatag gccttgttgt tttttgtttg ttttttttggg aaatactaga tacctttcag   8618
ctggcgttat atatatattt agtctttatt                                   8648
```

<210> SEQ ID NO 3
<211> LENGTH: 1096
<212> TYPE: PRT
<213> ORGANISM: Arabidopsis thaliana
<223> OTHER INFORMATION: EMBRYONIC FLOWER 1 (EMF1)

<400> SEQUENCE: 3

```
Met Gly Ser Ser Ile Lys Ile Asn Ser Ile Ser Ile Asp Leu Ala Gly
  1               5                  10                  15

Ala Ala Asn Glu Ile Asp Met Val Lys Cys Asp His Phe Ser Met Arg
                 20                  25                  30

Gly Phe Val Ala Glu Thr Arg Glu Arg Asp Leu Arg Lys Cys Trp Pro
             35                  40                  45

Phe Ser Glu Glu Ser Val Ser Leu Val Asp Gln Gln Ser Tyr Thr Leu
         50                  55                  60

Pro Thr Leu Ser Val Pro Lys Phe Arg Trp Trp His Cys Met Ser Cys
 65                  70                  75                  80

Ile Lys Asp Ile Asp Ala His Gly Pro Lys Asp Cys Gly Leu His Ser
                 85                  90                  95

Asn Ser Lys Ala Ile Gly Asn Ser Ser Val Ile Glu Ser Lys Ser Lys
            100                 105                 110

Phe Asn Ser Leu Thr Ile Ile Asp His Glu Lys Glu Lys Lys Thr Asp
        115                 120                 125

Ile Ala Asp Asn Ala Ile Glu Glu Lys Val Gly Val Asn Cys Glu Asn
    130                 135                 140

Asp Asp Gln Thr Ala Thr Thr Phe Leu Lys Lys Ala Arg Gly Arg Pro
145                 150                 155                 160

Met Gly Ala Ser Asn Val Arg Ser Lys Ser Arg Lys Leu Val Ser Pro
                165                 170                 175

Glu Gln Val Gly Asn Asn Arg Ser Lys Glu Lys Leu Asn Lys Pro Ser
            180                 185                 190

Met Asp Ile Ser Ser Trp Lys Glu Lys Gln Asn Val Asp Gln Ala Val
        195                 200                 205

Thr Thr Phe Gly Ser Ser Glu Ile Ala Gly Val Val Glu Asp Thr Pro
    210                 215                 220

Pro Lys Ala Thr Lys Asn His Lys Gly Ile Arg Gly Leu Met Glu Cys
225                 230                 235                 240

Asp Asn Gly Ser Ser Glu Ser Ile Asn Leu Ala Met Ser Gly Leu Gln
                245                 250                 255

Arg Arg Lys Ser Arg Lys Val Arg Leu Leu Ser Glu Leu Leu Gly Asn
            260                 265                 270

Thr Lys Thr Ser Gly Gly Ser Asn Ile Arg Lys Glu Glu Ser Ala Leu
        275                 280                 285

Lys Lys Glu Ser Val Arg Gly Arg Lys Arg Lys Leu Leu Pro Glu Asn
    290                 295                 300

Asn Tyr Val Ser Arg Ile Leu Ser Thr Met Gly Ala Thr Ser Glu Asn
```

```
              305                 310                 315                 320
         Ala Ser Lys Ser Cys Asp Ser Asp Gln Gly Asn Ser Glu Ser Thr Asp
                     325                 330                 335

Ser Gly Phe Asp Arg Thr Pro Phe Lys Gly Lys Gln Arg Asn Arg Arg
                     340                 345                 350

Phe Gln Val Val Asp Glu Phe Val Pro Ser Leu Pro Cys Glu Thr Ser
                     355                 360                 365

Gln Glu Gly Ile Lys Glu His Asp Ala Asp Pro Ser Lys Arg Ser Thr
                     370                 375                 380

Pro Ala His Ser Leu Phe Thr Gly Asn Asp Ser Val Pro Cys Pro Pro
         385                 390                 395                 400

Gly Thr Gln Arg Thr Glu Arg Lys Leu Ser Leu Pro Lys Lys Lys Thr
                     405                 410                 415

Lys Lys Pro Val Ile Asp Asn Gly Lys Ser Thr Val Ile Ser Phe Ser
                     420                 425                 430

Asn Gly Ile Asp Gly Ser Gln Val Asn Ser His Thr Gly Pro Ser Met
                     435                 440                 445

Asn Thr Val Ser Gln Thr Arg Asp Leu Leu Asn Gly Lys Arg Val Gly
                     450                 455                 460

Gly Leu Phe Asp Asn Arg Leu Ala Ser Asp Gly Tyr Phe Arg Lys Tyr
         465                 470                 475                 480

Leu Ser Gln Val Asn Asp Lys Pro Ile Thr Ser Leu His Leu Gln Asp
                     485                 490                 495

Asn Asp Tyr Val Arg Ser Arg Asp Ala Glu Pro Asn Cys Leu Arg Asp
                     500                 505                 510

Phe Ser Ser Ser Lys Ser Ser Gly Gly Trp Leu Arg Thr Gly
                     515                 520                 525

Val Asp Ile Val Asp Phe Arg Asn Asn Asn His Asn Thr Asn Arg Ser
         530                 535                 540

Ser Phe Ser Asn Leu Lys Leu Arg Tyr Pro Pro Ser Ser Thr Glu Val
         545                 550                 555                 560

Ala Asp Leu Ser Arg Val Leu Gln Lys Asp Ala Ser Gly Ala Asp Arg
                     565                 570                 575

Lys Gly Lys Thr Val Met Val Gln Glu His His Gly Ala Pro Arg Ser
                     580                 585                 590

Gln Ser His Asp Arg Lys Glu Thr Thr Thr Glu Glu Gln Asn Asn Asp
                     595                 600                 605

Asp Ile Pro Met Glu Ile Val Glu Leu Met Ala Lys Asn Gln Tyr Glu
                     610                 615                 620

Arg Cys Leu Pro Asp Lys Glu Glu Asp Val Ser Asn Lys Gln Pro Ser
         625                 630                 635                 640

Gln Glu Thr Ala His Lys Ser Lys Asn Ala Leu Leu Ile Asp Leu Asn
                     645                 650                 655

Glu Thr Tyr Asp Asn Gly Ile Ser Leu Glu Asp Asn Asn Thr Ser Arg
                     660                 665                 670

Pro Pro Lys Pro Cys Ser Ser Asn Ala Arg Arg Glu His Phe Pro
                     675                 680                 685

Met Gly Arg Gln Gln Asn Ser His Asp Phe Phe Pro Ile Ser Gln Pro
                     690                 695                 700

Tyr Val Pro Ser Pro Phe Gly Ile Phe Pro Pro Thr Gln Glu Asn Arg
         705                 710                 715                 720

Ala Ser Ser Ile Arg Phe Ser Gly His Asn Cys Gln Trp Leu Gly Asn
                     725                 730                 735
```

```
Leu Pro Thr Val Gly Asn Gln Asn Pro Ser Pro Ser Ser Phe Arg Val
            740                 745                 750
Leu Arg Ala Cys Asp Thr Cys Gln Ser Val Pro Asn Gln Tyr Arg Glu
        755                 760                 765
Ala Ser His Pro Ile Trp Pro Ser Ser Met Ile Pro Pro Gln Ser Gln
        770                 775                 780
Tyr Lys Pro Val Ser Leu Asn Ile Asn Gln Ser Thr Asn Pro Gly Thr
785                 790                 795                 800
Leu Ser Gln Ala Ser Asn Asn Glu Asn Thr Trp Asn Leu Asn Phe Val
                805                 810                 815
Ala Ala Asn Gly Lys Gln Lys Cys Gly Pro Asn Pro Glu Phe Ser Phe
            820                 825                 830
Gly Cys Lys His Ala Ala Gly Val Ser Ser Ser Ser Arg Pro Ile
            835                 840                 845
Asp Asn Phe Ser Ser Glu Ser Ser Ile Pro Ala Leu His Leu Leu Ser
        850                 855                 860
Leu Leu Asp Pro Arg Leu Arg Ser Thr Thr Pro Ala Asp Gln His Gly
865                 870                 875                 880
Asn Thr Lys Phe Thr Lys Arg His Phe Pro Pro Ala Asn Gln Ser Lys
                885                 890                 895
Glu Phe Ile Glu Leu Gln Thr Gly Asp Ser Ser Lys Ser Ala Tyr Ser
            900                 905                 910
Thr Lys Gln Ile Pro Phe Asp Leu Tyr Ser Lys Arg Phe Thr Gln Glu
        915                 920                 925
Pro Ser Arg Lys Ser Phe Pro Ile Thr Pro Ile Gly Thr Ser Ser
        930                 935                 940
Leu Ser Phe Gln Asn Ala Ser Trp Ser Pro His His Gln Glu Lys Lys
945                 950                 955                 960
Thr Lys Arg Lys Asp Thr Phe Ala Pro Val Tyr Asn Thr His Glu Lys
                965                 970                 975
Pro Val Phe Ala Ser Ser Asn Asp Gln Ala Lys Phe Gln Leu Leu Gly
            980                 985                 990
Ala Ser Asn Ser Met Met Leu Pro Leu Lys Phe His Met Thr Asp Lys
        995                 1000                1005
Glu Lys Lys Gln Lys Arg Lys Ala Glu Ser Cys Asn Asn Asn Ala Ser
    1010                1015                1020
Ala Gly Pro Val Lys Asn Ser Ser Gly Pro Ile Val Cys Ser Val Asn
1025                1030                1035                1040
Arg Asn Pro Ala Asp Phe Thr Ile Pro Glu Pro Gly Asn Val Tyr Met
                1045                1050                1055
Leu Thr Gly Glu His Leu Lys Val Arg Lys Arg Thr Thr Phe Lys Lys
            1060                1065                1070
Lys Pro Ala Val Cys Lys Gln Asp Ala Met Lys Gln Thr Lys Lys Pro
        1075                1080                1085
Val Cys Pro Pro Thr Gln Asn Ala
    1090                1095

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:ATP/GTP
      binding site motif or P-loop
<221> NAME/KEY: MOD_RES
```

-continued

```
<222> LOCATION: (1)
<223> OTHER INFORMATION: Xaa = Ala or Gly
<221> NAME/KEY: MOD_RES
<222> LOCATION: (2)..(5)
<223> OTHER INFORMATION: Xaa = any amino acid
<221> NAME/KEY: MOD_RES
<222> LOCATION: (8)
<223> OTHER INFORMATION: Xaa = Ser or Thr

<400> SEQUENCE: 4

Xaa Xaa Xaa Xaa Xaa Gly Lys Xaa
  1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:tyrosine
      kinase phosphorylation site
<221> NAME/KEY: MOD_RES
<222> LOCATION: (1)
<223> OTHER INFORMATION: Xaa = Arg or Lys
<221> NAME/KEY: MOD_RES
<222> LOCATION: (4)
<223> OTHER INFORMATION: Xaa = Asp or Glu
<221> NAME/KEY: MOD_RES
<222> LOCATION: (5)..(6)
<223> OTHER INFORMATION: Xaa = any amino acid

<400> SEQUENCE: 5

Xaa Val Val Xaa Xaa Xaa Tyr
  1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:tyrosine
      kinase phosphorylation site
<221> NAME/KEY: MOD_RES
<222> LOCATION: (1)
<223> OTHER INFORMATION: Xaa = Arg or Lys
<221> NAME/KEY: MOD_RES
<222> LOCATION: (4)
<223> OTHER INFORMATION: Xaa = Asp or Glu
<221> NAME/KEY: MOD_RES
<222> LOCATION: (5)..(7)
<223> OTHER INFORMATION: Xaa = any amino acid

<400> SEQUENCE: 6

Xaa Val Val Xaa Xaa Xaa Xaa Tyr
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:tyrosine
      kinase phosphorylation site
<221> NAME/KEY: MOD_RES
<222> LOCATION: (1)
<223> OTHER INFORMATION: Xaa = Arg or Lys
<221> NAME/KEY: MOD_RES
<222> LOCATION: (5)
<223> OTHER INFORMATION: Xaa = Asp or Glu
<221> NAME/KEY: MOD_RES
<222> LOCATION: (6)..(7)
<223> OTHER INFORMATION: Xaa = any amino acid

<400> SEQUENCE: 7
```

-continued

```
Xaa Val Val Val Xaa Xaa Xaa Tyr
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:tyrosine
      kinase phosphorylation site
<221> NAME/KEY: MOD_RES
<222> LOCATION: (1)
<223> OTHER INFORMATION: Xaa = Arg or Lys
<221> NAME/KEY: MOD_RES
<222> LOCATION: (5)
<223> OTHER INFORMATION: Xaa = Asp or Glu
<221> NAME/KEY: MOD_RES
<222> LOCATION: (6)..(8)
<223> OTHER INFORMATION: Xaa = any amino acid

<400> SEQUENCE: 8

Xaa Val Val Val Xaa Xaa Xaa Tyr
 1               5
```

NUCLEIC ACIDS ENCODING EMF1 THAT CONTROL REPRODUCTIVE DEVELOPMENT IN PLANTS

This application is a continuation-in-part of and claims the benefit of U.S. patent application Ser. No. 09/169,696, filed Oct. 9, 1998, now abandoned, the disclosure of which is incorporated by reference.

FIELD OF THE INVENTION

The present invention is directed to plant genetic engineering. In particular, it relates to modulation of expression of genes controlling reproductive development in plants.

BACKGROUND OF THE INVENTION

Arabidopsis primary shoots undergo a series of developmental phase changes as they mature and age (Schultz, et al., Development 119:745–765 (1993)). Their development can be broadly categorized into three major phases based on node morphologies: first, the rosette or vegetative phase, with nodes closely compressed and bearing a petiolated leaf and an axillary bud; second, the early-inflorescence phase, with nodes separated by internode elongation and bearing a sessile leaf and a coflorescence; and third, the late-inflorescence phase, with nodes bearing solitary flowers. Thus, two major phase transitions are involved in Arabidopsis main shoot development: the transition from rosette to early inflorescence when the rosette begins to bolt and the transition from early to late inflorescence (or from inflorescence to flower) when the primary shoot switches from producing cauline leaves and coflorescences to flowers. Ultimately, the primary shoot meristem becomes senescent and ceases producing flowers from its flanks (Shannon, et al., *Plant Cell* 3:877–892 (1991)).

The transition from rosette to early inflorescence is considered to be the vegetative-to-reproductive transition. It is regulated by many flowering-time genes, that is, floral repression and floral promotion genes (or early- and late-flowering genes, respectively) (Koornneef et al., *Mol. Gen. Genet*. 229:57–66 (1991); Zagofta, et al., *Aust. J. Plant Physiol*. 19:411–418 (1992)). Loss-of-function mutations in floral repression genes, such as EARLY FLOWER 1 (ELF1), cause early flowering, whereas mutations in floral promotion genes, such as CONSTANS (CO), delay transition from the rosette-to-inflorescence stage. In addition, two EMBRYONIC FLOWER (EMF) genes, EMF1 and EMF2, are proposed to be involved in this process as floral repressors, suppressing the onset of reproductive development (Sung et al., *Science* 258:1645–1647 (1992); Martinez-Zapater et al. In *Arabidopsis*, E. M. Meyerowitz and C. R. Somerville, eds (Cold Spring Harbor, N.Y.: Cold Spring Harbor Laboratory Press), pp 403–433 (1994); Castle, et al., *Flowering Newslet*. 19:12–19 (1995); Yang, et al., *Dev. Biol*. 169:421–435 (1995)). Based on this floral repressor concept, vegetatively growing plants must decrease EMF1 and EMF2 activities to initiate reproductive growth. It has been proposed that the floral repression genes maintain, whereas floral promotion genes inhibit, EMF1 and EMF2 activities. A balance of these gene actions would cause a gradual decline in EMF activities and determine the time of vegetative-to-reproductive transition.

The transition from inflorescence to flower is regulated by flower meristem identity genes, such as LEAFY (LFY), APETALA1 (AP1), AP2, and CAULIFLOWER (CAL) (Irish, et al., *Plant Cell* 2:741–753 (1990); Mandel, et al., *Nature* 360:273–277 (1992); Bowman, et al., *Development* 119:721–743 (1993); Jofuku, et al., *Plant Cell* 6:1211–1225 (1994)). Mutants with defective LFY, AP1, AP2, or AP1 CAL genes are impaired in flower initiation; thus, inflorescence-like or flowerlike shoots, instead of flowers, initiate peripherally from the apical meristem during the late-inflorescence phase. In addition to these genes, the TERMINAL FLOWER1 (TFL1) gene is reported to negatively regulate meristem identity gene function in inflorescence development. Both the primary shoot and the lateral shoots in tfl1 mutants terminate in a flower, reflecting a precocious inflorescence-to-flower transition (Alvarez et al., *Plant J.* 2:103–116 (1992)). Molecular data have shown that the LFY gene is ectopically expressed in the entire apical meristem of tfl1 primary and lateral shoots, which is consistent with the tfl1 phenotype (Bradley, et al., *Science* 275:80–83 (1997)). Thus, TFL1 functions to maintain inflorescence development. Mutants impaired in EMF1 or EMF2 produce a reduced inflorescence and a terminal flower, indicating a role for the EMF genes in delaying the inflorescence-to-flower transition.

The development of Arabidopsis floral organs also depends on normal EMF gene function. As in ap1 and ap2 mutants, weak emf mutants, such as emf1-1 and all of the emf2 mutants, lack petals (Yang, et al., Dev. Biol. 169:421–435 (1995)). The strong emf mutant, emf1-2, is impaired in the development of all floral organs: only carpelloid organs form. The effects of emf mutations on inflorescence and flower development suggest that EMF1 and EMF2 continue to function during reproductive development.

In light of the above, it is clear that EMF genes play an important role in reproductive development in plants. Control of the expression of the genes is therefore useful in controlling flowering and other functions in plants. These and other advantages are provided by the present application.

SUMMARY OF THE INVENTION

The present invention provides methods of modulating reproductive development (e.g., flowering and other traits) in plants. The methods involve providing a plant comprising a recombinant expression cassette containing an EMF1 nucleic acid linked to a plant promoter.

In some embodiments, expression of the EMF1 nucleic acids of the invention are used to enhance expression of an endogenous EMF1 gene or gene product activity. In these embodiments, the nucleic acids are used to inhibit or delay transition to a reproductive state and can be used to promote vegetative growth of the plant. Alternatively, transcription of the EMF1 nucleic acid inhibits expression of an endogenous EMF1 gene or the activity of the encoded protein. These embodiments are particularly useful in promoting the transition to a reproductive state and, for instance, promoting uniform flowering in plants.

In the expression cassettes, the plant promoter may be a constitutive promoter, for example, the CaMV 35S promoter. Alternatively, the promoter may be a tissue-specific or an inducible promoter. For instance, the promoter sequence from the EMF1 genes disclosed here can be used to direct expression in relevant plant tissues.

The invention also provides seed or fruit produced by the methods described above. The seed or fruit of the invention comprise a recombinant expression cassette containing an EMF1 nucleic acid.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

A "EMF1 nucleic acid" or "EMF1 polynucleotide sequence" of the invention is a subsequence or full length polynucleotide sequence of a gene which encodes a polypeptide involved in control of reproductive development and which, when mutated, promotes a transition to a reproductive state, e.g., flowering, in plants. An exemplary nucleic acid of the invention is the Arabidopsis EMF1 sequence disclosed below. EMF1 polynucleotides of the invention are defined by their ability to hybridize under defined conditions to the exemplified nucleic acids or PCR products derived from them. An EMF1 polynucleotide is typically at least about 30–40 nucleotides to about 3500 nucleotides, usually less than about 3000 nucleotides in length. The nucleic acids contain coding sequence of from about 100 to about 28000 nucleotides, often from about 500 to about 1000 nucleotides in length.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term EMF1 nucleic acid.

In the case where the inserted polynucleotide sequence is transcribed and translated to produce a functional polypeptide, one of skill will recognize that because of codon degenacy a number of polynucleotide sequences will encode the same polypeptide. These variants are specifically covered by the terms "EMF1 nucleic acid". In addition, the term specifically includes those sequences substantially identical (determined as described below) with an EMF1 polynucleotide sequence disclosed here and that encode polypeptides that are either mutants of wild type EMF1 polypeptides or retain the function of the EMF1 polypeptide (e.g., resulting from conservative substitutions of amino acids in the EMF1 polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., J. Mol. Biol. 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising EMF1 nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C. , and at least one wash in 0.2×SSC at a temperature of at least about 50° C. , usually about 55° C. to about 60° C. , for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DESCRIPTION OF THE PREFERRED EMBODIMENTS

Figure 1:
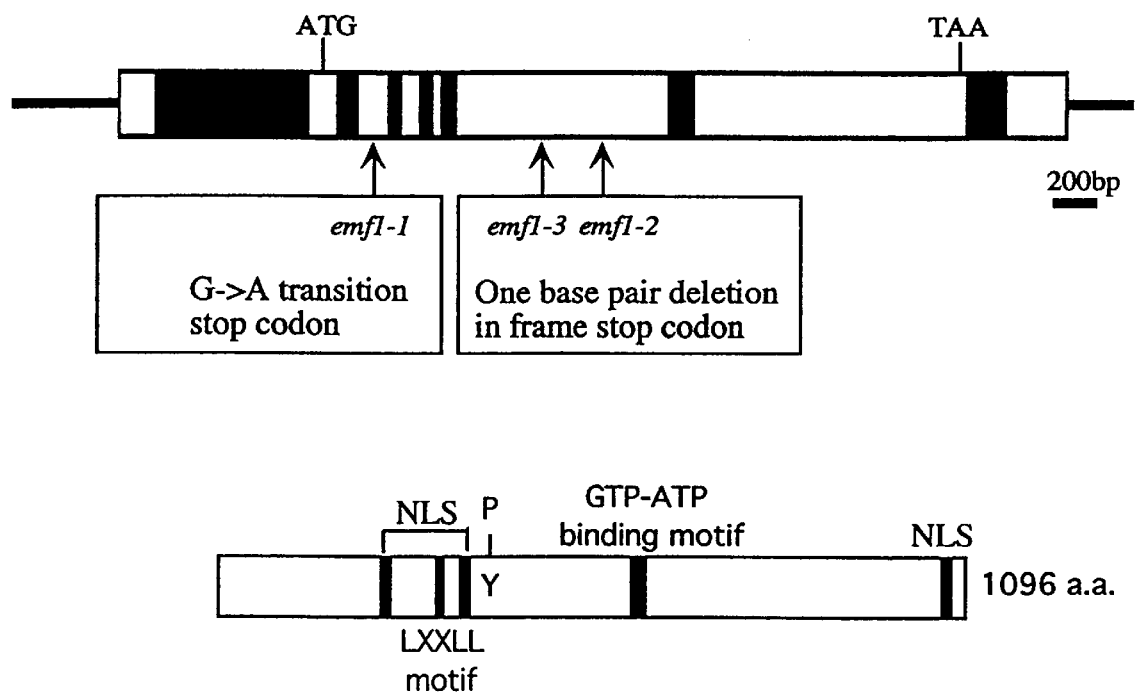
FIG. 1 is a diagram of the EMF1 locus in Arabidopsis.

This invention provides molecular strategies for controlling reproductive development, in particular flowering, in plants. The invention has wide application in agriculture, horticulture, and forestry. For example, enhanced expression of genes of the invention is useful to prevent flowering in grasses or vegetative crops, e.g., spinach, cabbage. Controlling or inhibiting expression of the genes is useful to promote early flowering in forest trees and agronomical crops or to ensure uniform flowering in various agronomic crops and ornamentals.

The present invention is based, at least in part, on the discovery of mutations, embryonic flowering (emf), and the subsequent cloning of the genes involved. A genetic model for the control of vegetative-to-reproductive transition has been proposed (Martinez-Zapater et al., *In Arabidopsis*, E. M. Meyerowitz and C. R. Somerville, eds (Cold Spring Harbor, N.Y.: Cold Spring Harbor Laboratory Press), pp. 403–433 (1994)). The main scheme of the model is that flowering is a default state and is negatively regulated by floral repressors. The hypothesis assumes that vegetative development is maintained as a result of the suppression of reproductive development. The EMF gene products are floral repressors because weak emf mutants produce an inflorescence directly after germination. For example, severe emf1 alleles cause the shoot to shift further into the reproductive state than do weak alleles, as evidenced by several distinct floral characteristics, including lack of stipules and trichomes on lateral organs, carpelloidy of lateral organs, direct development of a single flower or pistil, and precocious expression of floral genes (Chen et al. *The Plant Cell* 9:2011–2024 (1997)).

To flower, juvenile plants must acquire floral competence first (McDaniel, et al., *Dev. Biol.* 153:59–69 (1992)). Without wishing to be bound by theory it is proposed that the products of EMF1 genes, specify the level of floral competence, which must be abated to a level to enable the partial derepression of floral target genes for LFY to initiate flower development. In the absence of LFY, as in lfy and lfy ap1 plants, continued increase of floral competence would still occur, resulting in floral target gene expression and carpelloid organ formation.

Many observations indicate the existence of a gradient of "floral character" along the Arabidopsis inflorescence axis.

The gradient of floral character can also be seen on the shoots of other annual plants, such as tobacco (Tran, *Planta* 115:87–92 (197 3)). The common features seen in different plants suggest that the mechanism controlling plant shoot maturation may be a conserved one in angiosperms. This gradient effect may be interpreted as resulting from an increasing amount of floral activators or a decreasing amount of floral repressors during inflorescence development.

Without wishing to be bound by theory it is believed that the decline of floral repressor responsible for the vegetative-to-reproductive transition is also responsible for increasing the floral character during inflorescence development. For example, the differences in weak and strong emf1 phenotypes suggest that the extent of floral character corresponds with the EMF activity (Chen et al. *The Plant Cell* 9:2011–2024 (1997).

Epistasis of emf to floral repression and floral promotion mutations suggests that these floral genes act by modulating EMF activity to cause vegetative-to-inflorescence transition. Likewise, epistasis of emf1-2 to lfy-1, ap1-1, ap2-1, and ap1-1 cal suggests that EMF1 acts downstream from those floral genes in mediating the inflorescence-to-flower transition (Chen et al.). On the other hand, EMF appears to suppress floral genes. Therefore, there seems to be a reciprocal negative interaction between EMF and floral genes in controlling the development of Arabidopsis shoots from inflorescence to flower phase. This kind of interaction is consistent with the controllers of phase switching (COPS) hypothesis, which places EMF1 in the center of the COPS activity (Schultz, et al., *Development* 119:745–765 (1993)).

The COPS hypothesis holds that a high level of COPS activity suppresses reproductive development, allowing vegetative growth. If COPS activities continue to decline throughout the life span, the plant can progress from the rosette to inflorescence and to the flower phase. The reciprocal negative regulation between EMF and the floral genes provides a plausible mechanism for this hypothesis. During rosette growth, high EMF activity suppresses floral genes. EMF decline, mediated by the flowering-time genes, allows the activation of floral genes, which in turn suppress EMF activity, resulting in the sequential activation of other floral genes and the gradual decline of EMF activity during inflorescence and flower development.

Based on the above, it is clear that modulation of EMF1 activity can be used to control reproductive development in plants. Thus, isolated sequences prepared as described herein, can be used in a number of techniques, for example, to suppress or enhance endogenous EMF1 gene expression. Modulation of EMF1 gene expression or EMF1 activity in plants is particularly useful in controlling the transition from the vegetative to the reproductive state.

Isolation of EMF1 nucleic acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of EMF1 nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as ovules, and a cDNA library which contains the EMF1 gene transcript is prepared from the mRNA. Alternatively, cDNA may be prepared from mRNA extracted from other tissues in which EMF1 genes or homologs are expressed The cDNA or genomic library can then be screened using a probe based upon the sequence of a cloned EMF1 gene disclosed here. Probes may be used to hybridize with genomic DNA or cDNA sequences to isolate homologous genes in the same or different plant species. Alternatively, antibodies raised against an EMF1 polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the EMF1 genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: *A Guide to Methods and Applications*. (Innis, M, Gelfand, D., Sninsky, J. and White, T., eds.), Academic Press, San Diego (1990).

Appropriate primers and probes for identifying EMF1 sequences from plant tissues are generated from comparisons of the sequences provided here with other related genes. Using these techniques, one of skill can identify conserved regions in the nucleic acids disclosed here to prepare the appropriate primer and probe sequences. Primers that specifically hybridize to conserved regions in EMF1 genes can be used to amplify sequences from widely divergent plant species.

Standard nucleic acid hybridization techniques using the conditions disclosed above can then be used to identify full length cDNA or genomic clones.

Inhibition of EMF1 Activity or Gene Expression

Since EMF1 genes are involved in controlling reproduction, inhibition of endogenous EMF1 activity or gene expression is useful in a number of contexts. For instance, inhibition of expression is useful in promoting flowering in plants.

Inhibition of EMF gene expression

The nucleic acid sequences disclosed here can be used to design nucleic acids useful in a number of methods to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105: 125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al. *Plant Sci.* (Shannon) 127: 61–69 (1997)) and by preventing the accumulation of mRNA which encodes the protein of interest, (see, Baulcombe *Plant Mol. Bio.* 32:79–88 (1996); Prins and Goldbach *Arch. Virol.* 141: 2259–2276 (1996); Metzlaff et al. Cell 88: 845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous EMF1 gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress EMF1 gene expression. The targets can include, for instance, the coding regions, introns, sequences from exon/intron junctions, 5' or 3' untranslated regions, and the like.

Another well known method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22: 1067–1085 (1993); Flavell *Proc. Natl. Acad. Sci. USA* 91: 3490–3496 (1994); Stam et al. *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

Oligonucleotide-based triple-helix formation can also be used to disrupt EMF1 gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (Berlin) 75: 267–282 (1997)). Triple helix DNAs can be used to target the same sequences identified for antisense regulation.

Catalytic RNA molecules or ribozymes can also be used to inhibit expression of EMF1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251 (1997); and Haseloff et al., *Nature*, 334:585–591 (1988).

Modification of endogenous EMF1 genes

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Alternatively, homologous recombination can be used to induce targeted gene disruptions by specifically deleting or altering the EMF1 gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an EMF1 gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered EMF1 gene expression in transgenic plants. The mutated gene will interact with the target wild-type gene in such a way that homologous recombination and targeted replacement of the wild-type gene will occur in transgenic plant cells, resulting in suppression of EMF1 activity.

Alternatively, oligonucleotides composed of a contiguous stretch of RNA and DNA residues in a duplex conformation with double hairpin caps on the ends can be used. The RNA/DNA sequence is designed to align with the sequence of the target EMF1 gene and to contain the desired nucleotide change. Introduction of the chimeric oligonucleotide on an extrachromosomal T-DNA plasmid results in efficient and specific EMF1 gene conversion directed by chimeric molecules in a small number of transformed plant cells. This method is described in Cole-Strauss et al. *Science* 273:1386–1389(1996) and Yoon et al. *Proc. Natl. Acad. Sci. USA* 93: 2071–2076 (1996).

The endogenous EMF1 genes can also be inactivated using recombinant DNA techniques by transforming plant cells with constructs comprising transposons or T-DNA sequences. The emf1 mutants prepared by these methods are identified according to standard techniques.

Other means for inhibiting EMF activity

EMF1 activity may be modulated by eliminating the proteins that are required for EMF1 cell-specific gene expression. Thus, expression of regulatory proteins and/or the sequences that control EMF1 gene expression can be modulated using the methods described here.

Another strategy is to inhibit the ability of an EMF1 protein to interact with itself or with other proteins. This can be achieved, for instance, using antibodies specific to EMF1. In this method cell-specific expression of EMF1 -specific antibodies is used to inactivate functional domains through antibody:antigen recognition (see, Hupp et al. *Cell* 83:237–245 (1995)). Alternatively, dominant negative mutants of EMF1 can be prepared. Use of dominant negative mutants to inactivate target genes is described in Mizukami et al. *Plant Cell* 8:831–845 (1996).

Use of Nucleic Acids of the Invention to Enhance EMF1 Gene Expression

Isolated sequences prepared as described herein can also be used to introduce expression of a particular EMF1 nucleic acid to enhance or increase endogenous gene expression. For instance, enhanced expression can be used to increase vegetative growth by preventing the plant from making the transition from vegetative to a reproductive state. Where overexpression of a gene is desired, the desired gene from a different species may be used to decrease potential sense suppression effects.

One of skill will recognize that the polypeptides encoded by the genes of the invention, like other proteins, have different domains which perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of recombinant vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1' or 2' promoter derived from T-DNA of *Agrobacterium tumafaciens*, and other transcription initiation regions from various plant genes known to those of skill. Such genes include for example, ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from Brassica napus (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of the EMF1 nucleic acid in a specific tissue or may be otherwise under more precise environmental or developmental control. Examples of environmental conditions that may effect transcription by inducible promoters include anaerobic conditions, elevated temperature, or the presence of light. Alternatively, promoter sequences from genes in which expression is controlled by exogenous compounds can be used. For instance, the promoters from glucocorticoid receptor genes can be used (Aoyama and Chau, *Plant J* 11:605–12 (1997)). Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in the vegetative shoot apex are particularly useful in the present invention. Examples of suitable tissue specific promoters include the promoter from LEAFY (Weigel et al. *Cell* 69:843–859 (1992)).

In addition, the promoter sequences from the EMF1 genes disclosed here can be used to drive expression of the EMF1 polynucleotides of the invention or heterologous sequences. The sequences of the promoters are identified below.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of transgenic plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983). In planta transformation procedures can also be used (Bechtold, et al., (1993). *Comptes Rendus de l'Academie des Sciences Serie III Sciences de la Vie*, 316: 1194–1199).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof Such regeneration techniques are described generally in Klee et al. *Ann. Rev. of Plant Phys*. 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Beta, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Papaver, Persea, Phaseolus, Picea, Pinus, Pistachia, Pisum, Pyrus, Prunus, Raphanus, Ricinus, Rosa, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. If antisense or other techniques are used to control gene expression, Northern blot analysis can be used to screen for desired plants. In addition, the timing or other characteristics of reproductive development can be detected. Plants can be screened, for instance, for early flowering. Similarly, if EMF1 gene expression is enhanced, the plants can be screened for continued vegetative growth. These procedures will depend, part on the particular plant species being used, but will be carried out according to methods well known to those of skill.

EXAMPLE 1

The following example describes the positional cloning of an EMF1 gene of the invention.

The EMF1 locus was mapped to the upper arm of chromosome 5, near 20cM, within an interval of less than 1.5 cM between the molecular markers g6833 and g6830 (Yang et al. *Dev. Biol.* 169:421–435 (1995)). A Yeast Artificial Chromosome (YAC) clone contig spanning this region was constructed based on published information as well as our own hybridization data. Results obtained from mapping the ends of different YAC clones relative to EMF1 locus showed that the gene resides on the CIC7A7 YAC clone, 2 recombinants away from the right end of yUP18G5 (18G5-R) and 5 recombinants from the CIC9G2 right end (9G2-R). Hence, the 9G2-R and 18G5-R end fragments were used as the closest flanking makers for initiating a chromosome walk from both directions. We screened existing cosmid and lambda genomic libraries, cosmid libraries of the CIC7A7 YAC DNA, and a P1/TAC clone contig spanning the region of CIC7A7, and conducted the further walking to construct a contig consisted of cosmid, lambda, P1 and TAC clone that covers the region from the 18G5-R end to the 9G2-R end. Using polymorphic fragments within these clones to monitor the progress of the chromosome walk towards EMF1 locus, we determined that the EMF1 is located on the cosmid clone CD82.

The genomic DNA from CD82 clone was subcloned into pBluescript vector and sequenced (SEQ ID NO:1). The analysis of CD82 sequence, using DNA Strider program, revealed three ORFs (ORF1, 2, and 3). To define the EMF1 gene among the three ORFs, we mapped the ORF3 using an 1.5 kb BamH1 insert. One recombinant breakpoint was found between EMF1 and the 1.5 kb fragment, ruling out ORF3 as a candidate for EMF1 gene. Based on sequence comparison, we found that ORF2 has homology to gulono-lactone oxiase (23% identities and 41% similarities, gulono-lactone oxidase from rattus norvegicus (Nishikimi et al., J. Biol. Chem. 267:21967 (1992) and the Diminuto-like proteins (22% identity and 47% similarity, Wilson et al., Nature 368:32–38 (1994); Takahashi et al., *Genes Development* 9:97 (1995)). We sequenced the ORF1 gene from plants homozygous for three different emf1 alleles (emf1-1, em1 -2 and emf1-3) and identified a frame shift mutation in each of the three alleles (FIG. 1). These frameshift mutations would have resulted in truncated polypeptides. A deletion of 1 base was found at position 2402, 1344, and 941, leading to a truncated protein in emf1-1, 1–2, and 1–3, respectively. The fact that all 3 mutants have a mutation in ORF1 that results in truncated polypetides and that the severity of the mutant phenotypes corresponds with the increased truncation of the polypeptides lead us to conclude that ORF1 is EMF1.

Structural analysis of the EMF1 gene was carried out (SEQ ID NOs:2 and 3). The exon/intron organization of the EMF1 gene was analyzed using NetPlantGene v : 2.0 program (Hebsgaard, et al., *Nucleic Acids Research*, 24:3439–3452 (1996)). The EMF1 gene consists of 8 exons and 4 introns, and the deduced protein is 1069 amino acid long. The sequence comparison using BLAST program against all Arabidopsis GenBank DNA including EST and BAC ends reveals two ESTs with sequence identity to the EMF1 gene. Clone VBVLF01 (from Versailles-VB Arabidopsis thaliana cDNA library, Accession number: Z46543) has 100% identity to EMF1 and clone F2A4T7 (from CD4–14 Arabidopsis thaliana cDNA library, Accession number: N96450) 95%; both are partial cDNA sequences. The comparison using BLAST Program against all non-redundant GenBank CDS translations+PDB+SwissProt+PIR+PRF or dbest (Non-redundant Database of GenBank+EMBL+DDBJ EST Divisions) give no significant similarity to known genes in any organisms, indicating the novelty of the EMF1 gene sequence.

PSORT program was used to predict the subcellular localization of the EMF1 protein. There are two types of nuclear localization signals, both were found in the EMF1 gene. The first type, consisted of three 4 residue patterns composed of basic amino acids (K or R), or three basic amino acids (K or R) and H or P, was found at three positions within the EMF1 protein, i.e., position 295, 412, and 1071. The second type of nuclear targeting signal (Robbins et al., *Cell*, 64:615(1991)), composed of 2 basic residues, 10 residue spacer, and another basic region consisting of at least 3 basic residues out of 5 residues, was found at three different positions, i.e., 171, 282, and 1071, of the EMF 1 protein. Futhermore, the basic residues (K and R) represent 18% of the weight of the protein. This evidence indicates that EMF1 protein is localized in the nucleus.

An ATP/GTP binding site motif A or P- loop ([AG]-X(4)-G-K-[ST]) (SEQ. ID No. 4) appears at position 573 in the EMF1 protein. A tyrosine kinase phosphorylation site ([RK]-V(2,3)- [DE]-X(2,3)-Y) (SEQ ID NOS:5–8) appears at position 299 in the protein. The LXXLL motif has been proposed to be a signature sequence that facilitates the interaction of different proteins with nuclear receptors (Heery et al. *Nature*, 387:733 (1997)) was found at position 266. In plants, it has been identified in the RGA protein (a putative transcriptional regulator that represses the gibberellic acid (GA) response, Silverstone et al., *Plant Cell*, 10: 155 (1998). Another feature of the putative EMF 1 protein is the high content in serine residues (S) that represent 10% of the molecular weight, with homopolymeric regions of serine. Taken together the molecular characteristics suggest that EMF1 protein is a novel, transcriptional regulator involved in the flowering signaling pathway.

The above example is provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated nucleic acid molecule comprising an EMF1 polynucleotide sequence, which polynucleotide sequence
    (a) specifically hybridizes to SEQ ID NO:2 following a hybridization step in a buffer of 40% formamide, 1 M NaCl, 1% SDS at 37° C. followed by one wash in 0.2×SSC at 50° C. for 20 minutes; and
    (b) promotes early transition from a vegetative state to a reproductive state in a plant when the polynucleotide is operably linked to a plant promoter to inhibit EMF1 gene expression and introduced into a plant.

2. The isolated nucleic acid molecule of claim 1, wherein the EMF1 polynucleotide is at least 100 nucleotides in length.

3. The isolated nucleic acid molecule of claim 1, wherein the EMF1 polynucleotide is SEQ ID NO:2.

4. The isolated nucleic acid molecule of claim 1, further comprising a plant promoter operably linked to the EMF1 polynucleotide.

5. The isolated nucleic acid molecule of claim 4, wherein the plant promoter is from a EMF1 gene.

6. The isolated nucleic acid of claim 4, wherein the EMF1 polynucleotide is linked to the promoter in an antisense orientation.

7. An isolated nucleic acid molecule comprising an EMF1 polynucleotide sequence, which polynucleotide sequence encodes an EMF1 polypeptide as shown in SEQ ID NO:3.

8. A transgenic plant comprising an expression cassette comprising a plant promoter operably linked to a heterologous EMF1 polynucleotide of claim 1.

9. The transgenic plant of claim 8, wherein the heterologous EMF1 polynucleotide encodes a EMF1 polypeptide.

10. The transgenic plant of claim 9, wherein the EMF 1 polypeptide is as shown in SEQ ID NO:3.

11. The transgenic plant of claim 8, wherein the heterologous EMF1 polynucleotide is linked to the promoter in an antisense orientation.

12. The transgenic plant of claim 8, wherein the plant promoter is from an EMF1 gene.

13. The transgenic plant of claim 8, wherein the EMF1 gene is as shown in SEQ ID NO:2.

14. A method of promoting early transition from a vegetative state to a reproductive state in a plant, the method comprising introducing into the plant an expression cassette comprising a plant promoter operably linked to a heterologous EMF 1 polynucleotide.

15. The method of claim 14, wherein the heterologous EMF1 polynucleotide encodes an EMF1 polypeptide.

16. The method of claim 14, wherein the EMF1 polypeptide has an amino acid sequence as shown in SEQ ID NO:3.

17. The method of claim 14, wherein the heterologous EMF1 polynucleotide is linked to the promoter in an antisense orientation.

18. The method of claim 14, wherein the heterologous EMF1 polynucleotide is SEQ ID NO:2.

19. The method of claim 14, wherein the plant promoter is from a EMF1 gene.

20. The method of claim 14, wherein the expression cassette is introduced into the plant through a sexual cross.

21. An isolated nucleic acid molecule comprising a polynucleotide sequence encoding a polypeptide at least 80% identical to SEQ ID NO: 3, wherein the polynucleotide promotes early transition from a vegetative state to a reproductive state in a plant when the polynucleotide is operably linked to a plant promoter to inhibit EMF1 gene expression and introduced into a plant.

22. The isolated nucleic acid of claim 21, wherein the polypeptide is at least 95% identical to SEQ ID NO:3.

23. A recombinant expression cassette comprising a plant promoter operably linked to the polynucleotide sequence of claim 21.

24. The recombinant expression cassette of claim 23, wherein the promoter is constitutive.

25. The recombinant expression cassette of claim 23, wherein the promoter is tissue-specific.

26. The recombinant expression cassette of claim 23, wherein the polypeptide is at least 95% identical to SEQ ID NO:3.

27. A transgenic plant comprising the recombinant expression cassette of claim 21.

* * * * *